United States Patent
Breu et al.

(10) Patent No.: US 6,197,959 B1
(45) Date of Patent: Mar. 6, 2001

(54) PIPERIDINE DERIVATIVES

(75) Inventors: Volker Breu, Schliengen (DE); Daniel Bur; Hans-Peter Märki, both of Basel (CH); Eric Vieira, Allschwil (CH); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/542,598

(22) Filed: Apr. 4, 2000

(30) Foreign Application Priority Data

Apr. 27, 1999 (EP) .................................... 99108200

(51) Int. Cl.$^7$ ........................ A61K 31/47; C07D 215/02; C07D 215/00
(52) U.S. Cl. .......................... 546/165; 546/166; 514/314
(58) Field of Search .................... 546/165, 166; 514/314

(56) References Cited

U.S. PATENT DOCUMENTS 6,051,712 * 4/2000 Binggeli .

FOREIGN PATENT DOCUMENTS

WO 97/09311 3/1997 (WO) .

OTHER PUBLICATIONS

Kaslow, C.E. et al., J. Am. Chem. Soc., 77, p 1054–1055 (1955).
Fischli, W. et al., Hypertension, 18 (1), pp 22–31 (1991).
Clozel, J.–P. et al., Hypertension, 22 (1), pp 9–17 (1993).
Pals, D. T. et al., Hypertension, 8, pp 1105–1112 (1986).
Dellaria J. F. et al., J. Med. Chem., 30, pp 2137–2144 (1987).
Kokubu T. et al., Biochem. Biophys. Res. Commun., 118, pp 929–933 (1984).
Capson, T.L. et al., J. Org. Chem., 53 (25) pp 5903–5908 (1988).

* cited by examiner

Primary Examiner—D. Margaret Seaman
(74) Attorney, Agent, or Firm—George W. Johnston; William H. Epstein; John P. Parise

(57) ABSTRACT

Compounds of formula (I)

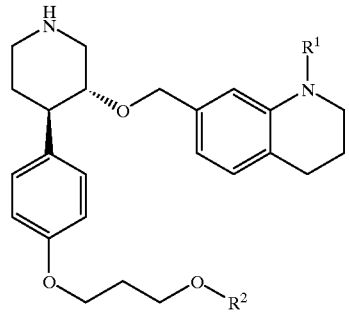

I wherein $R^1$ and $R^2$ are as defined in the description and claims and pharmaceutically acceptable salts thereof, are useful for the treating diseases associated with restenosis, glaucoma, cardiac infarct, high blood pressure and end organ damage, for example, cardiac insufficiency and kidney insufficiency.

113 Claims, No Drawings

PIPERIDINE DERIVATIVES

BACKGROUND OF THE INVENTION

The present invention relates to novel piperidine derivatives, their manufacture and use as medicaments.

SUMMARY OF THE INVENTION

The subject invention provides compounds of the formula:

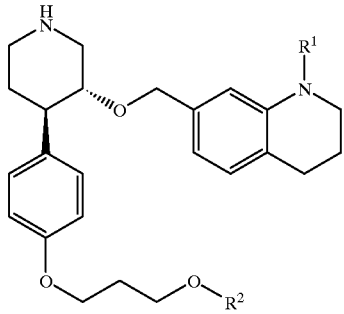

I wherein
$R^1$ is
a) $-(CH_2)_k-N(R^3,R^4)$, wherein k is 2, 3 or 4;
b) $-(CH_2)_k-O-R^3$, wherein k is 2, 3 or 4;
c) $-(CH_2)_m-R^5$, wherein m is 1 or 2; or
d) $-(CH_2)_l-R^6$, wherein l is 1, 2 or 3;

$R^2$ is lower cycloalkylalkyl, 1,1,1-trifluoroethyl, phenyl, benzyl, phenyl substituted independently with from one to three halogen, cyano, $C_1-C_3$-alkoxy, or nitro groups, or benzyl substituted independently with from one to three halogen, cyano, $C_1-C_3$-alkoxy, or nitro groups;

$R^3$ is hydrogen or $C_1-C_3$-alkyl;

$R^4$ is hydrogen, $C_1-C_3$-alkyl, $C_1-C_3$-alkylsulfonyl, aminosulfonyl, $C_1-C_3$-alkylaminosulfonyl, $C_1-C_3$-alkylaminocarbonyl, $C_1-C_3$-alkylcarbonyl, trifluoromethylcarbonyl, trifluoromethylsulfonyl, or aminocarbonyl;

$R^5$ is $C_1-C_3$-alkoxycarbonyl, aminocarbonyl, $C_1-C_3$-alkylaminocarbonyl, di-$C_1-C_3$-alkylaminocarbonyl, or cyano;

$R^6$ is imidazolyl or triazolyl, with the proviso that 1 must be 2 or 3 if the imidazolyl or triazolyl is bound via a C—N-bond;

and pharmaceutically acceptable salts thereof.

While the substituents are above listed collectively, all combinations of the mentioned substituents are enabled and described. For example, $R^1$ can be $-(CH_2)_k-N(R^3,R^4)$, wherein k is 2, 3 or 4; or $-(CH_2)_k-O-R^3$, wherein k is 2, 3 or 4; or $-(CH_2)_m-R^5$, wherein m is 1 or 2; or d) $-(CH_2)_l-R^6$, wherein l is 1, 2 or 3. A preferred example of $R^1$ being $-(CH_2)_2-N(R^3,R^4)$ is ethylacetamide.

In a preferred $R^1$ group, $R^3$ is hydrogen or $C_1-C_3$-alkyl, such as methyl or ethyl. Favorably, when $R^1$ is $-(CH_2)_k-O-R^3$, the specific group is $-(CH_2)_2-O-R^3$ or $-(CH_2)_3-O-R^3$, such as methoxypropyl or hydroxypropyl.

As mentioned above, $R^2$ can be lower cycloalkylalkyl, 1,1,1-trifluoroethyl, phenyl, benzyl, phenyl substituted independently with from one to three halogen, cyano, $C_1-C_3$-alkoxy, or nitro groups, or benzyl substituted independently with from one to three halogen, cyano, $C_1-C_3$-alkoxy, or nitro groups. One preferred selection is where $R^2$ is benzyl or benzyl substituted independently with from one to three halogen, cyano, $C_1-C_3$-alkoxy, or nitro groups. Favorably, $R^2$ is benzyl substituted with one $C_1-C_3$-alkoxy group or benzyl substituted independently with one $C_1-C_3$-alkoxy group and from one to three halogen. Especially preferred is methoxybenzyl, and more specifically 2-methoxybenzyl Preferred groupings of $R^4$ include hydrogen or $C_1-C_3$-alkyl and $C_1-C_3$-alkylsulfonyl, aminosulfonyl, $C_1-C_3$-alkylaminosulfonyl, $C_1-C_3$-alkylaminocarbonyl, $C_1-C_3$-alkylcarbonyl, trifluoromethylcarbonyl, trifluoromethylsulfonyl, or aminocarbonyl. Further preferred groupings include where $R^4$ is $C_1-C_3$-alkylsulfonyl, aminosulfonyl, $C_1-C_3$-alkylcarbonyl, trifluoromethylcarbonyl, trifluoromethylsulfonyl, or aminocarbonyl, or where $R^4$ is methanesulfonyl, aminosulfonyl, acetyl, trifluoroacetyl, trifluoromethanesulfonyl, or aminocarbonyl. Favored is where $R^4$ is $C_1-C_3$-alkylcarbonyl, such as acetyl.

Another preferred group is where $R^5$ is $C_1-C_3$-alkoxycarbonyl, aminocarbonyl, $C_1-C_3$-alkylaminocarbonyl, di-$C_1-C_3$-alkylaminocarbonyl, or cyano, or aminocarbonyl.

Another preferred group is where $R^6$ is imidazolyl, with the proviso that 1 must be 2 or 3 if the imidazolyl is bound via a C—N-bond or where $R^6$ is triazolyl, with the proviso that 1 must be 2 or 3 if the triazolyl is bound via a C—N-bond.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention relates to novel piperidine derivatives of formula I

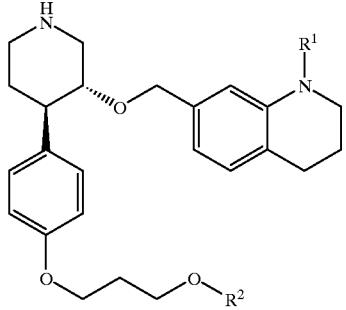

I wherein
$R^1$ is
a) $-(CH_2)_k-N(R^3,R^4)$ and wherein k is 2, 3 or 4;
b) $-(CH_2)_k-O-R^3$, wherein k is 2, 3 or 4;
c) $-(CH_2)_m-R^5$, wherein m is 1 or 2; or
d) $-(CH_2)_l-R^6$, wherein l is 1, 2 or 3;

$R^2$ is lower cycloalkylalkyl, 1,1,1-trifluoroethyl, phenyl or benzyl, wherein the phenyl or benzyl groups optionally are independently substituted with 1–3 halogen, cyano, $C_1-C_3$-alkoxy or nitro;

$R^3$ is hydrogen or $C_1-C_3$-alkyl;

$R^4$ is hydrogen, $C_1-C_3$-alkyl, $C_1-C_3$-alkylsulfonyl, aminosulfonyl, $C_1-C_3$-alkylaminosulfonyl, $C_1-C_3$-alkylaminocarbonyl, $C_1-C_3$-alkylcarbonyl, trifluoromethylcarbonyl, trifluoromethylsulfonyl, aminocarbonyl;

$R^5$ is $C_1$–$C_3$-alkoxycarbonyl, aminocarbonyl, $C_1$–$C_3$-alkylaminocarbonyl, di-$C_1$–$C_3$-alkylaminocarbonyl or cyano;

$R^6$ is imidazolyl or triazolyl; with the proviso that l is 2 or 3 if imidazolyl or triazolyl is bound via a C—N-bond;

and pharmaceutically acceptable salts thereof.

The present invention also relates to pharmaceutical compositions comprising a compound of formula (I) and a pharmaceutically acceptable carrier and/or adjuvant.

The piperidine derivatives of the present invention have an inhibitory activity on the natural enzyme renin. They can accordingly be used for the treatment of disorders which are associated with restenosis, glaucoma, cardiac infarct, high blood pressure and end organ damage, e.g. cardiac insufficiency and kidney insufficiency. Accordingly, the present invention relates to a method for the prophylactic and/or therapeutic treatment of diseases which are associated with restenosis, glaucoma, cardiac infarct, high blood pressure and end organ damage, e.g. cardiac insufficiency and kidney insufficiency, which method comprises administering a compound of formula (I) to a human being or an animal. Furthermore, the present invention relates to the use of such compounds for the preparation of medicaments for the treatment of disorders which are associated with restenosis, glaucoma, cardiac infarct, high blood pressure and end organ damage, e.g. cardiac insufficiency and kidney insufficiency.

The present invention also relates to processes for the preparation of the compounds of formula (I).

WO 97/09311 discloses piperidine derivatives. However, these tetrahydroquinoline compounds display low in vitro potencies.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "alkyl" refers to a branched or straight chain monovalent saturated aliphatic hydrocarbon radical of one to twenty carbon atoms, preferably one to sixteen carbon atoms.

The term "lower alkyl" refers to a branched or straight chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atom(s), preferably 3 to 6 carbon atoms.

The term "cycloalkylalkyl" refers to a branched or straight chain monovalent saturated aliphatic carbon radical of 1 to 5, preferably 1 to 4 carbon atom(s) having a monovalent carbocyclic radical of 3 to 10 carbon atom(s), preferably 3 to 6 carbon atoms.

The term "halogen" refers to fluorine, chlorine, bromine and iodine, with fluorine and chlorine being preferred.

The term "alkoxy" refers to the group R'—O—, wherein R' is an alkyl.

The term "alkylsulfonyl" refers to the group —$SO_2$—R', wherein R' is lower alkyl.

The term "aminosulfonyl-" refers to the group $NH_2$—$SO_2$—.

The term "alkylaminosulfonyl" refers to the group R'—NH—$SO_2$—wherein R' is alkyl.

The term "alkylaminocarbonyl" refers to the group R'—NH—C(O)—, wherein R' is alkyl.

The "term alkylcarbonyl" refers to the group R'—C(O)—, wherein R' is alkyl.

The term "aminocarbonyl" refers to the group $H_2N$—C(O)—.

The term "alkoxycarbonyl" refers to the group R'—C(O)—, wherein R' is an alkoxy.

The term "di-alkylaminocarbonyl" refers to the group R'R"N—C(O)—, wherein R' and R" are alkyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms.

In detail, the present invention refers to compounds of formula (I)

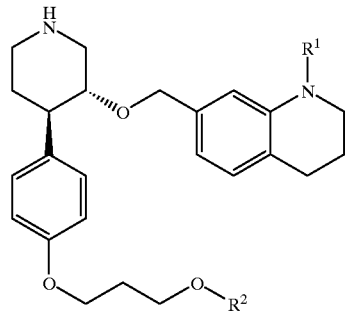

I wherein $R^1$ is
a) —$(CH_2)_k$—$N(R^3,R^4)$ and wherein k is 2, 3 or 4;
b) —$(CH_2)_k$—O—$R^3$, wherein k is 2, 3 or 4;
c) —$(CH_2)_m$—$R^5$, wherein m is 1 or 2; or
d) —$(CH_2)_l$—$R^6$, wherein l is 1, 2 or 3;

$R^2$ is lower cycloalkylalkyl, 1,1,1-trifluoroethyl, phenyl or benzyl, wherein the phenyl or benzyl groups optionally are independently substituted with 1–3 halogen, cyano, $C_1$–$C_3$-alkoxy or nitro;

$R^3$ is hydrogen or $C_1$–$C_3$-alkyl;

$R^4$ is hydrogen, $C_1$–$C_3$-alkyl, $C_1$–$C_3$-alkylsulfonyl, aminosulfonyl, $C_1$–$C_3$-alkylaminosulfonyl, $C_1$–$C_3$-alkylaminocarbonyl, $C_1$–$C_3$-alkylcarbonyl, trifluoromethylcarbonyl, trifluoromethylsulfonyl, aminocarbonyl;

$R^5$ is $C_1$–$C_3$-alkoxycarbonyl, aminocarbonyl, $C_1$–$C_3$-alkylaminocarbonyl, di-$C_1$–$C_3$-alkylaminocarbonyl or cyano;

$R^6$ is imidazolyl or triazolyl; with the proviso that l is 2 or 3 if imidazolyl or triazolyl is bound via a C—N-bond;

and pharmaceutically acceptable salts thereof.

The compounds of formula (I) have at least two asymmetric carbon atoms and can exist in the form of optically pure enantiomers or as racemates, in which the relative configuration of the two piperidine ring substitutents has to be trans as shown in formula (I). The invention embraces all of these forms.

More particularly, the present invention relates to compounds of the above formula (I), wherein $R^1$ is —$(CH_2)_k$—$N(R^3,R^4)$, preferably —$(CH_2)_2$—$N(R^3,R^4)$. Even more preferably, $R^1$ is ethylacetamide. The preferred residue $R^3$ for these species is hydrogen.

In a further preferred embodiment of the present invention $R^1$ is —$(CH_2)_k$—O—$R^3$ wherein k is 2, 3 or 4, more preferably compounds wherein $R^1$ is —$(CH_2)_2$—O—$R^3$ or —$(CH_2)_3$—O—$R^3$, even more preferably —$(CH_2)_3$—O—$R^3$, e.g. compounds wherein $R^1$ is methoxypropyl or hydroxypropyl. The preferred residue $R^3$ for these species is hydrogen and $C_1$–$C_3$-alkyl, more preferably hydrogen and methyl.

Moreover, the present invention relates to compounds wherein $R^2$ is benzyl optionally substituted with a group independently selected from 1–3 halogens, cyano, $C_1$–$C_3$-alkoxy or nitro, preferably, $R^2$ is benzyl optionally substituted with a group independently selected from 1–3 $C_1$–$C_3$-alkoxy, e.g. methoxy, and more preferably substituted with one $C_1$–$C_3$-alkoxy group, e.g. a methoxy group. In a preferred embodiment, the above substituent, e.g. a methoxy group, in ortho position to the substituent providing the connection with the phenylpiperidine of the compounds of formula (I).

In a further preferred embodiment of the present invention $R^2$ is benzyl substituted with 1–3 $C_1$–$C_3$-alkoxy groups and 1–3 halogens. Preferably, the benzyl group is substituted by one $C_1$–$C_3$-alkoxy group and 1–3 halogens. In a more preferred embodiment, the alkoxy group is methoxy and is in ortho position to the substituent providing the connection with the phenylpiperidine of the compounds of formula (I), and the halogen is fluorine.

In another preferred embodiment, $R^4$ is $C_1$–$C_3$-alkylsulfonyl, aminosulfonyl, $C_1$–$C_3$-alkylcarbonyl, trifluoromethylcarbonyl, trifluoromethylsulfonyl, aminocarbonyl or $C_1$–$C_3$-alkylcarbonyl, more preferably methanesulfonyl, aminosulfonyl, acetyl, trifluoroacetyl, trifluoromethanesulfonyl or aminocarbonyl, even more preferably $C_1$–$C_3$-alkylcarbonyl, and most preferably acetyl.

In an additional preferred embodiment, $R^5$ is cyano or aminocarbonyl and $R^6$ is imidazolyl.

The invention especially discloses compounds of formula (I) and pharmaceutically acceptable salts thereof, selected from 1. (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide;
2. (3R,4R)-[7-(4-[4-[3-(2-methoxy-benzyloxy)-propoxy]-phenyl]-piperidin-3-yloxymethyl)-3,4-dihydro-2H-quinolin-1-yl]-acetic acid ethyl ester;
3. (3R,4R)-2-[7-[4-[4-[3-(2-methoxy-benzyloxy)-propoxy]-phenyl]-piperidin-3-yloxymethyl-3,4-dihydro-2H-quinolin-1-yl]-acetamide;
4. (3R,4R)-3-[7-[4-[4-[3-(2-methoxy-benzyloxy)-propoxy]-phenyl]-piperidin-3-yloxymethyl]-3,4-dihydro-2H-quinolin-1-yl]-propan-1-ol;
5. (3R,4R)-2-[7-[4-[4-[3-(2-methoxy-benzyloxy)-propoxy]-phenyl]-piperidin-3-yloxymethyl]-3,4-dihydro-2H-quinolin-1-yl]-ethanol;
6. (3R,4R)-[7-(4-[4-[3-(2-methoxy-benzyloxy)-propoxy]-phenyl]-piperidin-3-yloxymethyl)-3,4-dihydro-2H-quinolin-1-yl]-acetic acid methyl ester;
7. (3R,4R)-3-[7-(4-[4-[3-(2-methoxy-benzyloxy)-propoxy]-phenyl]-piperidin-3-yloxymethyl)-3,4-dihydro-2H-quinolin-1-yl]-propionic acid methyl ester;
8. (3R,4R)-[3-[7-[4-[4-[3-(2-methoxy-benzyloxy)-propoxy]-phenyl]-piperidin-3-yloxymethyl]-3,4-dihydro-2H-quinolin-1-yl]-propyl]-methyl-amine;
9. (3R,4R)-[2-[7-[4-[4-[3-(2-methoxy-benzyloxy)-propoxy]-phenyl]-piperidin-3-yloxymethyl]-3,4-dihydro-2H-quinolin-1-yl]-ethyl]-methyl-amine;
10. (3R,4R)-3-[7-(4-[4-[3-(2-methoxy-benzyloxy)-propoxy]-phenyl]-piperidin-3-yloxymethyl)-3,4-dihydro-2H-quinolin-1-yl]-propylamine
11. (3R,4R )-N-[3-[7-(4-[4-[3-(2-methoxy-benzyloxy)-propoxy]-phenyl]-piperidin-3-yloxymethyl)-3,4-dihydro-2H-quinolin-1-yl]-propyl]-acetamide;
12. (3R,4R)-4-[7-(4-[4-[3-(2-methoxy-benzyloxy)-propoxy]-phenyl]-piperidin-3-yloxymethyl)-3,4-dihydro-2H-quinolin-1-yl]-butylamine;
13. (3R,4R)-1-(2-imidazol-1-yl-ethyl)-7-(4-[4-[3-(2-methoxy-benzyloxy)-propoxy]-phenyl]-piperidin-3-yloxymethyl)-1,2,3,4-tetrahydro-quinoline;
14. (3R,4R)-7-[4-[4-[3-(2-methoxy-benzyloxy)-propoxy]-phenyl]-piperidin-3-yloxymethyl]-1-(3-methoxy-propyl]-1,2,3,4-tetrahydro-quinoline;
15. (3R,4R)-2-[7-[4-[4-[3-(2-methoxy-benzyloxy)-propoxy]-phenyl]-piperidin-3-yloxymethyl]-3,4-dihydro-2H-quinolin-1-yl]-ethylamine;
16. (3R,4R)-[7-(4-[4-[3-(2-methoxy-benzyloxy)-propoxy]-phenyl]-piperidin-3-yloxymethyl)-3,4-dihydro-2H-quinolin-1-yl]-acetonitrile;
17. (3R,4R)-7-[4-[4-[3-(2-methoxy-benzyloxy)-propoxy]-phenyl]-piperidin-3-yloxymethyl]-1-(2-methoxy-ethyl)-1,2,3,4-tetrahydro-quinoline;
18. (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-methanesulfonamide;
19. (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-sulfamide;
20. (3R,4R)-[2-[7-(4-[4-[3-(2-methoxy-benzyloxy)-propoxy]-phenyl]-piperidin-3-yloxymethyl)-3,4-dihydro-2H-quinolin-1-yl]-ethyl]-dimethyl-amine;
21. (3R,4R)-[[2-[7-[4-[4-[3-(2-methoxy-benzyloxy)-propoxy]-phenyl]-piperidin-3-yloxymethyl]-3,4-dihydro-2H-quinolin-1-yl]-ethyl]-urea;
22. (3R,4R)-2,2,2-trifluoro-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide;
23. (3R,4R)-7-[4-[4-(3-cyclopropylmethoxy-propoxy)-phenyl]-piperidin-3-yloxymethyl]-1-(3-methoxy-propyl)-1,2,3,4-tetrahydro-quinoline; and
24. (3R,4R)-1-(3-methoxy-propyl)-7-[4-[4-[3-(2,2,2-trifluoro-ethoxy)-propoxy]-phenyl]-piperidin-3-yloxymethyl]-1,2,3,4-tetrahydro-quinoline;

and pharmaceutically acceptable salts thereof.

An especially preferred compound is (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide and pharmaceutically acceptable salts thereof.

Other especially preferred compounds are (3R,4R)-3-[7-[4-[4-[3-(2-methoxy-benzyloxy)-propoxy]-phenyl]-piperidin-3-yloxymethyl]-3,4-dihydro-2H-quinolin-1-yl]-propan-1-ol and (3R,4R)-7-[4-[4-[3-(2-methoxy-benzyloxy)-propoxy]-phenyl]-piperidin-3-yloxymethyl)-1-(3-methoxy-propyl]-1,2,3,4-tetrahydro-quinoline and pharmaceutically acceptable salts thereof.

The invention also relates to pharmaceutical compositions comprising a compound as defined above and a pharmaceutically acceptable carrier and/or adjuvant. The pharmaceutical compositions may comprise in addition one or more compounds active against restenosis, glaucoma, cardiac infarct, high blood pressure and end organ damage, e.g. cardiac insufficiency and kidney insufficiency. Examples for these additional compounds are angiotensin converting enzyme-inhibitors, e.g. captopril, lisinopril, enalapril and cilazapril; angiotensin-(1)-receptor antagonists, e.g. lorsartan and valsartan; diuretica, e.g. hydrochlorothiazide, mefrusid and furosemid; endothelin receptor antagonists, e.g. bosentan; endothelin converting enzyme inhibitors or neutral endopeptidase inhibitors; calcium channel blockers (antagonists), e.g. nifedipine, verapamil, and diltiazem; nitrates, e.g. glyceroltrinitrates (nitroglycerin) and isosorbid-dinitrates; beta-receptor blockers, e.g. carvedilol, alprenolol and propranolol; alpha-1 adrenoceptor antagonists, e.g. prazosin and terazosin; and reserpin.

A further embodiment of the present invention refers to the use of a compound as defined above for the preparation of medicaments comprising a compound as defined above for the treatment or prophylaxis of restenosis, glaucoma, cardiac infarct, high blood pressure and end organ damage, e.g. cardiac insufficiency and kidney insufficiency.

An additional embodiment of the invention relates to a method for the prophylactic and/or therapeutic treatment of disorders in which renin plays a significant pathological role, especially restenosis, glaucoma, cardiac infarct, high blood pressure and end organ damage, e.g. cardiac insufficiency and kidney insufficiency which method comprises administering a compound as defined above to a human being or an animal.

The compounds as defined above may be manufactured by cleaving off the protecting group from a compound of formula (II)

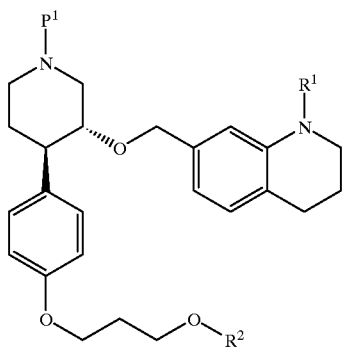

in which $P^1$ represents a protecting group and the remaining symbols have the significance given above.

The cleavage of a protecting group $P^1$ can be carried out in a manner known per se. Examples of protecting groups $P^1$ are usual amino protecting groups such as tert-butoxycarbonyl, benzyloxycarbonyl, allyloxycarbonyl, vinyloxycarbonyl, alkylsilylalkyloxycarbonyl such as 2-(trimethylsilyl)ethoxycarbonyl, and trichloroethoxycarbonyl.

The cleavage of these protecting groups may be effected by acidic or basic hydrolysis, by reductive methods or by means of Lewis acids or fluoride salts. A solution of a mineral acid such as hydrochloric acid, hydrobromic acid, sulfuric acid, phosphoric acid and the like in an inert solvent or solvent mixture is advantageously used for the acidic hydrolysis. Suitable solvents are alcohols such as methanol or ethanol, ethers such as tetrahydrofuran or dioxan, chlorinated hydrocarbons such as methylene chloride, and the like. Alkali metal hydroxides and alkali metal carbonates such as potassium hydroxide or sodium hydroxide or potassium carbonate or sodium carbonate, organic amines such as piperidine, and the like can be used for the basic hydrolysis. Inert organic solvents as referred to above for the acidic hydrolysis can be used as solubilizers. The reaction temperature for the acidic and basic hydrolysis can be varied in a range from 0° C. to the reflux temperature, with the reaction preferably being carried out at between about 0° C. and room temperature. The tert-butoxycarbonyl group is conveniently cleaved off with hydrochloric acid, hydrogen chloride, trifluoroacetic acid or formic acid in the presence or absence of an inert solvent. Furthermore, the tert-butoxycarbonyl group can be cleaved off by means of anhydrous zinc bromide in the presence of an inert solvent, preferably methylene chloride. The cleavage of the trichloroethoxycarbonyl group can be advantageously effected reductively with zinc in glacial acetic acid. The reaction temperature can lie in a range of 0° C. to 40° C., with the reaction preferably being carried out at room temperature. The cleavage of the 2-(trimethylsilyl)ethoxycarbonyl group can be effected by means of fluoride ions in the presence of an inert solvent such as acetonitrile, dimethyl sulphoxide, dimethylformamide or tetrahydrofuran, preferably by means of tetrabutylammonium fluoride in tetrahydrofuran, at temperatures from about 0° C. to about room temperature.

Compounds of formula (II) may be prepared according to the following scheme:

Scheme I

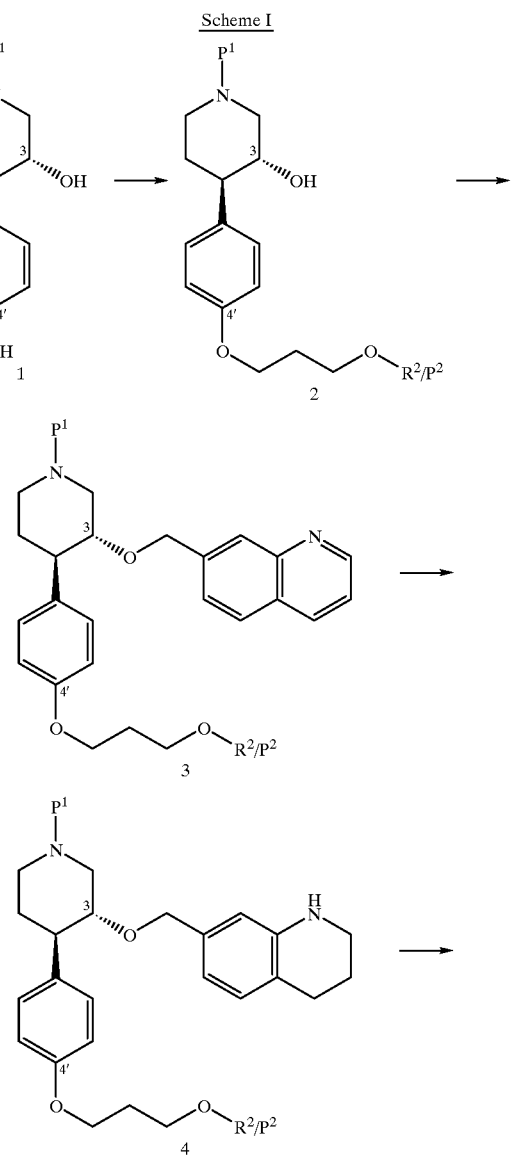

-continued

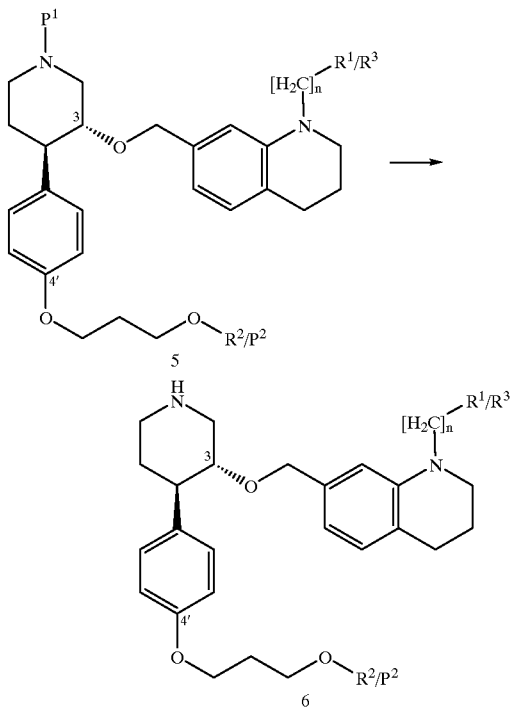

Compounds of formula 1 have been described in WO97/09311 and can be used as starting material for the preparation of compounds of formula 2. The linkage of the group—(CH$_2$)$_3$—O—R$^2$/P$^2$ can be effected selectively by reaction with a derivative of the group to be introduced which carries a suitable leaving group, although the desired group can also be built up stepwise or can contain suitably protected functional groups (P$^2$), which allow further structural modifications at a later stage of the synthesis. Chlorides, bromides, iodides, tosylates or mesylates come into consideration as alkylating agents. The selective linkage with the phenolic alcohol is effected according to alkylation methods which are known per se in the presence of a base such as potassium carbonate in a solvent which is inert under the reaction conditions, such as e.g. an ether such as tetrahydrofuran or 1,2-dimethoxyethane, or polar solvents such as N,N-dimethylformamide, dimethylsulfoxide, acetone, methyl-ethyl-ketone or pyridine at temperatures between 0° C. and 140° C.

Compounds of formula 3 and 4 can be obtained from 2 by alkylation with a suitable quinoline or tetrahydroquinoline derivative carrying a methylene group in position 7 functionalized with a leaving group, like a bromide, chloride, a tosyloxy or a mesyloxy group. The alkylation of the secondary alcohol is effected according to methods known per se, for example in a solvent which is inert under the reaction conditions such as in ether solvents, like tetrahydrofuran or 1,2-dimethoxyethane, or in N,N-dimethylformamide or dimethylsulfoxide, in the presence of an alcoholate-forming base, like sodium hydride or potassium tert-butoxide, at temperatures between 0° C. and 40° C. As alkylating agents can be used a suitable quinoline or tetrahydroquinoline derivative carrying, a methylene group in position 7 functionalized with a leaving group, like a bromide, chloride, a tosyloxy or a mesyloxy group. As suitable quinoline derivative can be used preferably 7-bromomethyl-quinoline hydrobromide [J. Am. Chem. Soc. 77, 1054 (1955)]. In the case of tetrahydroquinoline derivatives as alkylating agents the nitrogen may be substituted by a protecting group or by a substituent as finally desired or suitable as intermediate.

Quinoline derivatives of formula 3 can be reduced to tetrahydroquinoline derivatives of formula 4 using sodium borohydride in the presence of a nickel(II)- or a cobalt(II)-salt in an alcoholic solution, e.g. in methanol or in ethanol, at temperatures between 0° C. and 40° C.

In case that the 4'-substituent introduced contains a protective function P$^2$ and does not represent the final substituent desired, the protective function, e.g. a tetrahydropyranyl group, can be removed after introduction of the quinolinylmethyl unit. The deprotected primary alcohol may then be transformed into a tosylate, a mesylate or a suitable halide and reacted with an alcoholate like cyclopropylmethanolate or trifluoroethanolate in an ether solvent, like tetrahydrofuran, or in N,N-dimethylformamide or dimethylsulfoxide giving the desired 4'-substituent.

N-alkylation of the tetrahydroquinoline moiety in compounds of formula 4 can be performed with an alkylating agent such as a halo, tosyloxy- or mesyloxy-alkanol or alkyl ether, a halo-acetic ester, a-halo-acetic amide, a halo-acetonitrile, a halo-propionic ester or a halo-N-alkyl-amide in the presence of a base like sodium hydride, disodiumhydrogen phosphate, sodium carbonate or triethylamine, in solvents like toluene, tetrahydrofuran, N,N-dimethylformamide, dimethylsulfoxide, acetone, methyl-ethyl-ketone, N-methyl-pyrrolidone or pyridine at temperatures between 0° C. and 140° C., and eventually in the presence of catalysts which can be inorganic iodide salts such as sodium iodide, lithium iodide, preferably potassium iodide, or organic iodide salts such as tetramethylammonium- or tetrabutylammonium iodide.

The alkylating agents used can either contain the whole substituent desired or optionally suitably protected functional groups, which allow further structural modifications at a later stage of the synthesis. Further structural variations can comprise i) reduction of a nitrile function to an amino function or ii) transformation of an alcohol into an amine or an azide. The reduction of the nitrile can be effected using sodium borohydride in the presence of a nickel(II)- or a cobalt(II)-salt in an alcohol solvent, such as methanol or ethanol, at temperatures between 0° C. and 40° C. The resulting amine can be object of a further derivatization by methods well known in the literature, e.g. by transformation into an amide, a sulfonamide, a urea or a sulfonyl urea derivative. The transformation of an alcohol into an amine or an azide can be effected by transformation of the alcohol into a halide, mesylate or tosylate and thereafter substitution by a primary, secondary or tertiary amine or substitution by an azide group, which subsequently can be reduced to a primary amine by methods well known in the literature.

Final removal of the Boc-protecting group P$^1$ can be performed in the presence of acids, such as hydrochloric, hydrobromic, sulfuric, phosphoric, trifluoroacetic acid in a variety of solvents, such as alcohols and alcohol/water mixtures, ethers and chlorinated hydrocarbons. The Boc-protecting group can also be removed with anhydrous zinc bromide in inert solvents, such as dichloromethane or 1,2-dichloroethane.

Accordingly, the present invention comprises a process as described above comprising the reaction of a compound of formula 1

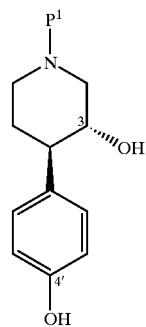

1 wherein $P^1$ is as defined above with an activated derivative of formula —$(CH_2)_3$—$R^2/P^2$ wherein $R^2$ is as defined above and $P^2$ is a protecting group of $R^2$; followed by the reaction of the resulting compound of formula 2

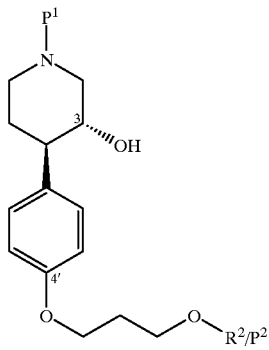

2 with an activated quinoline or tetrahydroquinoline derivative carrying a methylene group in position 7 and optionally reduction of the quinoline product resulting in a compound of formula 4,

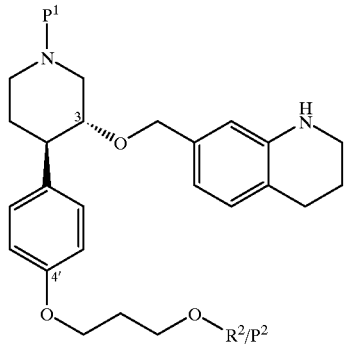

4 followed by N-alkylation of a compound of formula 4 with an alkylating agent to give a compound of formula 5

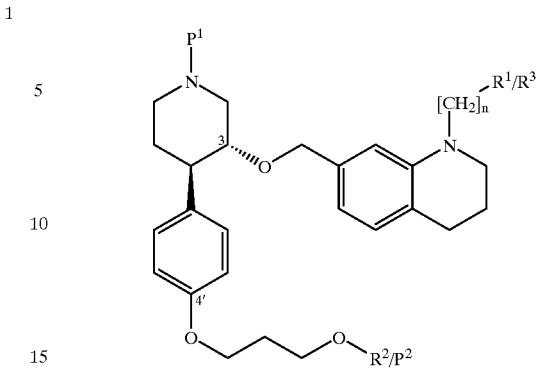

5 wherein —$(CH_2)_n$—$R^1/R^3$ represents $R^1$ as defined above optionally carrying an additional protecting group, and optionally followed by cleaving off any protecting groups to give compounds of formula (I) as defined above.

Starting compounds 1 are known in the art and may be prepared according to the methods described in WO97/09311 or according to the following reaction:

Compounds of formula 7

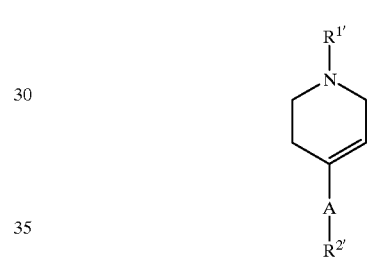

7 wherein A is arylene, e.g. phenyl; $R^{1'}$ is —$C^*R^{3'}R^{4'}R^{5'}$; $R^{2'}$ is —O-alkyl, —O-cycloalkyl, —O-alkenyl, —O-aryl, —O-aralkyl, —O-aralkoxyalkyl, —O-alkylsulfonyl, —O-arylsulfonyl, chlorine, bromine or iodine; $R^{3'}$ is hydrogen; $R^{4'}$ is aryl; $R^{5'}$ is alkyl, cycloalkyl, aryl, alkoxyalkyl or hydroxyalkyl; and $C^*$ is an asymmetric carbon atom; are hydroborated to give compounds of formula 8

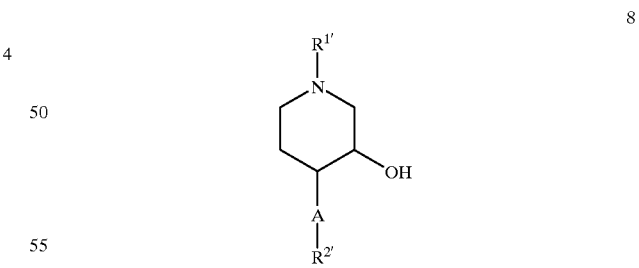

8 optionally followed by isolation of the desired stereoisomer. The hydroboration reaction can be effected like any of the hydroboration reactions which are known in the art for example with achiral or chiral hydroboration reagents. Preferred examples of such compounds are $NaBH_4/BF_3.Et_2O$, $BH_3$-THF, $BH_3$-dimethylsulfide complex, $BH_3$-triethylamine complex, 9-borabicyclo(3.3.1)-nonane and isopinocampheyl-borane or a chemical equivalent of anyone of the mentioned compounds. Particularly preferred is the above process, wherein a compound of the formula 2 is reacted with $NaBH_4/BF_3.Et_2O$, $BH_3$-THF or isopinocampheyl borane. Most preferred are $NaBH_4/BF_3.Et_2O$ and isopinocampheyl borane. Finally the chiral auxiliary group $R^{1'}$ and an $R^{2'}$ ether function can be cleaved by known methods described in the literature such as hydrogenolysis. The piperidine moiety can than be protected with a protecting group $P^1$ as described above.

The present invention relates to all compounds of formula (I), as prepared by one of the processes described above.

The invention also relates to compounds as defined above for the treatment of diseases which are associated with high blood pressure and cardiac insufficiency, as well as glaucoma, cardiac infarct, kidney insufficiency and restenosis.

The compounds of formula (I) and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angiotensin II increases blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to that of the heptapeptide angiotensin III which is formed therefrom as a cleavage product. Inhibitors of the enzymatic activity of renin bring about a decrease in the formation of angiotensin I and as a consequence of this the formation of a smaller amount of angiotensin II. The reduced concentration of this active peptide hormone is the direct reason for the blood pressure-lowering activity of renin inhibitors.

The in vitro potency of renin inhibitors can, as described by W. Fischli et al. in Hypertension, Vol. 18 (1), 22–31 (1991) or Hypertension Vol. 22 (1), 9–17 (1993) be demonstrated experimentally by means of the tests described hereinafter. The tests can be carried out in analogy to those described by D. T. Pals et al. in Hypertension Vol. 8, 1105–1112 (1986) or J. Boger et al. in J. Med. Chem. 28, 1779–1790 (1985) or J. F. Dellaria et al. in J. Med. Chem. 30, 2137–2144 (1987) or T. Kokubu et al. in Biochem. Biophys. Res. Commun. 118, 929–993 (1984):

In vitro Test With Pure Human Renin

The test is carried out in Eppendorf test tubes. The incubation mixture consists of (1) 100 μl of human renin in buffer A (0.1 M sodium phosphate solution, pH 7.4, containing 0.1% bovine serum albumin, 0.1% sodium aside and 1 mM ethylenediaminetetraacetic acid), sufficient for a renin activity of 2–3 ng of angiotensin I/ml/hr.; (2) 145 μl of buffer A: (3) 30 μl of 10 mM human tetradecapeptide renin substrate (hTD) in 10 mM hydrochloric acid: (4) 15 μl of dimethyl sulphoxide with or without inhibitor and (5) 10 μl of a 0.03 molar solution of hydroxyquinoline sulphate in water.

The samples are incubated for three hours at 37° C. and, respectively, 4° C. in triplicate. 2×100 μl samples per test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH) 0.09%. The production of angiotensin I is determined by the difference between the test at 37° C. and that at 4° C.

The following controls are carried out:

(a) Incubation of hTD samples without renin and without inhibitor at 37° C. and 4° C. The difference between these two values gives the base value of the angiotensin I production.

(b) Incubation of hTD samples with renin, but without inhibitor at 37° C. and 4° C. The difference between these values gives the maximum value of the angiotensin I production.

In each sample the base value of the angiotensin I production is subtracted from the angiotensin I production which is determined. The difference between the maximum value and the base value gives the value of the maximum substrate hydrolysis (=100%) by renin.

The results are given as $IC_{50}$ values which denote the concentration of the inhibitor at which the enzymatic activity is inhibited by 50%. The $IC_{50}$ values are determined from a linear regression curve from a logit-log plot.

The results obtained in this test are compiled in the following table:

TABLE

| Compound | $IC_{50}$ values in nMol/l |
| --- | --- |
| A | 0.05 |
| B | 0.05 |
| C | 0.08 |
| D | 0.02 |
| E | 0.04 |
| F | 0.05 |
| G | 0.07 |
| H | 0.07 |
| I | 0.06 |
| J | 0.09 |
| K | 0.05 |

A = (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide;
B = (3R,4R)-[7-(4-[4-[3-(2-methoxy-benzyloxy)-propoxy]-phenyl]-piperidin-3-yloxymethyl)-3,4-dihydro-2H-quinolin-1-yl]-acetic acid ethyl ester;
C = (3R,4R)-3-[7-[4-[4-[3-(2-methoxy-benzyloxy)-propoxy]-phenyl]-piperidin-3-yloxymethyl]-3,4-dihydro-2H-quinolin-1-yl]-propan-1-ol;
D = (3R,4R)-[7-(4-[4-[3-(2-methoxy-benzyloxy)-propoxy]-phenyl]-piperidin-3-yloxymethyl)-3,4-dihydro-2H-quinolin-1-yl]-acetic acid methyl ester;
E = (3RS,4R)-3-[7-(4-[4-[3-(2-methoxy-benzyloxy)-propoxy]-phenyl]-piperidin-3-yloxymethyl)-3,4-dihydro-2H-quinolin-1-yl]-propionic acid methyl ester;
F = (3R,4R)-7-[4-[4-[3-(2-methoxy-benzyloxy)-propoxy]-phenyl]-piperidin-3-yloxymethyl)-1-(3-methoxy-propyl]-1,2,3,4-tetrahydro-quinoline;
G = (3R,4R)-[7-(4-[4-[3-(2-methoxy-benzyloxy)-propoxy]-phenyl]-piperidin-3-yloxymethyl)-3,4-dihydro-2H-quinolin-1-yl]-acetonitrile;
H = (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-methanesulfonamide;
I = (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-sulfamide;
J = (3R,4R)-[[2-[7-[4-[4-[3-(2-methoxy-benzyloxy)-propoxy]-phenyl]-piperidin-3-yloxymethyl]-3,4-dihydro-2H-quinolin-1-yl]-ethyl]-urea;
K = (3R,4R)-2,2,2-trifluoro-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide.

It will be appreciated that the compounds of formula (I) in this invention may be derivatised at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters and pivaloyloxymethyl esters. Additionally, any physiologically acceptable equivalents of the compounds of formula (I), similar to the metabolically labile esters, which are capable of producing the parent compounds of formula (I) in vivo, are within the scope of this invention.

As mentioned earlier, medicaments containing a compound of formula (I) are also an object of the present invention, as is a process for the manufacture of such medicaments, which process comprises bringing one or more compounds of formula (I) and, if desired, one or more other therapeutically valuable substances into a galenical administration form.

The pharmaceutical compositions may be administered orally, for example in the form of tablets, coated tablets, dragées, hard or soft gelatine capsules, solutions, emulsions or suspensions. Administration can also be carried out rectally, for example using suppositories; locally or percutaneously, for example using ointments, creams, gels or solutions; or parenterally, e.g,. intravenously, intramuscularly, subcutaneously, intrathecally or transdermally, using, for example injectable solutions. Furthermore, administration can be carried out sublingually or as opthalmological preparations or as an aerosol, for example in the form of a spray.

For the preparation of tablets, coated tablets, dragees or hard gelatine capsules the compounds of the present invention may be admixed with pharmaceutically inert, inorganic or organic excipients. Examples of suitable excipients for tablets, dragées or hard gelatine capsules include lactose, maize starch or derivatives thereof, talc or stearic acid or salts thereof.

Suitable excipients for use with soft gelatine capsules include for example vegetable oils, waxes, fats, semi-solid or liquid polyols etc.; according to the nature of the active ingredients it may however be the case that no excipient is needed at all for soft gelatine capsules.

For the preparation of solutions and syrups, excipients which maybe used include for example water, polyols, saccharose, invert sugar and glucose.

For injectable solutions, excipients which may be used include for example water, alcohols, polyols, glycerine, and vegetable oils.

For suppositories, and local or percutaneous application, excipients which may be used include for example natural or hardened oils, waxes, fats and semi-solid or liquid polyols.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

It is a prerequisite that all adjuvants used in the manufacture of the preparations are non-toxic.

Intravenous, intramuscular or oral administration is a preferred form of use. The dosages in which the compounds of formula (I) are administered in effective amounts depend on the nature of the specific active ingredient, the age and the requirements of the patient and the mode of application. In general, daily dosages of about 1 mg–1000 mg, preferably 10 mg–300 mg, per day come into consideration.

The following Examples shall illustrate preferred embodiments of the present invention but are not intended to limit the scope of the invention.

EXAMPLES

Example 1

(a) A solution of 16.50 g (56.24 mmol) of (3R,4R)-3-hydroxy-4-(4-hydroxy-phenyl)-piperidine-1-carboxylic acid tert-butyl ester in 40 ml of N,N-dimethylformamide was treated in succession with 12.68 g (59.06 mmol) of 1-(3-chloro-propoxymethyl)-2-methoxy-benzene (WO 97/09311) and 12.44 g (90.00 mmol) of potassium carbonate. This mixture was stirred at 120° C. for 26 hours. Subsequently, the salts were filtered off and washed with dichloromethane. The filtrate was concentrated in a high vacuum to eliminate most of the N,N-dimethylformamide, poupred into 300 ml of an ice/water mixture and the aqueous phase was extracted three times with 100 ml of dichloromethane. The combined organic phases were washed once with a small amount of water, dried over magnesium sulphate, evaporated under reduced pressure and dried in a high vacuum. The thus-obtained crude product (31.64 g) was separated on silica gel using a 99:1 mixture of dichloromethane and methanol as the eluent and yielded 25.4 g (53.85 mmol, 95.8% of theory) of (3R,4R)-3-hydroxy-4-[4-[3-(2-methoxy-benzyloxy)-propoxy]-phenyl]-piperidine-1-carboxylic acid tert-butyl ester as a slightly yellow oil; MS: 489 $(M+NH_4^+)^+$.

(b) 3.40 g (7.20 mmol) of (3R,4R)-3-hydroxy-4-[4-[3-(2-methoxy-benzyloxy)-proposy]-phenyl]-piperidine-1-carboxylic acid tert-butyl ester and 2.18 g (7.20 mmol) of 7-bromomethyl-quinoline hydrobromide (1:1) [J. Am. Chem. Soc. 77, 1054(1955)] were dissolved in 50 ml of absolute N,N-dimethylformamide under argon and then 0.83 g (19.0 mmol) of sodium hydride dispersion (55% in mineral oil) was added at room temperature in small portions. Subsequently, the mixture was stirred at room temperature for 16 hours. The reaction mixture was poured onto ice-water, the product was extracted 3 times with ethyl acetate, the combined organic phases were washed twice with distilled water, then dried over magnesium sulphate, filtered and concentrated. The crude product (5.2 g, yellow oil) was chromatographed on silica gel with ethyl acetate/hexane 2:1 to yield 3.77 g (6.15 mmol, 85.4% of theory) of (3R,4R)-4-[4-[3-(2-methoxy-benzyloxy)-propoxy]-phenyl]-3-(quinolin-7-yl-methoxy)-piperidine-1-carboxylic acid tert-butyl ester as a colorless oil; MS: 613 $(M+H)^+$.

(c) 3.77 g (6.15 mmol) of (3R,4R)-4-[4-[3-(2-methoxy-benzyloxy)-propoxy]-phenyl]-3-(quinolin-7-yl-methoxy)-piperidin-1-carboxylic acid tert-butyl ester and 0.73 g (3.08 mmol, 0.5 equiv.) of nickel(II) chloride hexahydrate were dissolved in 50 ml of methanol. 0.93 g (24.8 mmol) of sodium borohydride was added at 0° C. in small portions over a period of 30 minutes. The resulting black suspension was then stirred for 1 hour at 0° C., and 2 hours at room temperature. The reaction mixture was slowly poured into a vigorously stirred mixture of 150 ml 5% ammonium chloride solution and 400 ml of ether. After further stirring for 30 minutes, the organic phase was separated. The slightly blue aqueous phase was further extracted 5 times with 50 ml of ether. The combined organic phases were washed twice with distilled water, then dried over magnesium sulphate, filtered and concentrated. The crude product (3.2 g, yellow oil) was chromatographed on silica gel with ethyl acetate/hexane 1:1 to yield 2.92 g (4.73 mmol, 77.0% of theory) of (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester as a colorless oil; MS: 617 $(M+H)^+$.

(d) A solution of 2.07 g (3.36 mmol) of (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester in 6 ml of acetonitrile was treated successively with 0.82 g (6.72 mmol, 2.0 equiv.) of N-2-chloroethyl acetamide, 0.53 g (5.04 mmol, 1.5 equiv.) of anhydrous sodium carbonate, and 0.056 g (0.34 mmol, 0.1 equiv.) of potassium iodide. This mixture was refluxed for 48 hours. Subsequently, it was poured into 100 ml of an ice/water mixture and extracted three times with 50 ml of ethyl acetate. The combined organic phases were washed three times with 20 ml of water, dried over magnesium sulphate, evaporated under reduced pressure and dried in a high vacuum. The thus-obtained crude product was separated on silica gel using ethyl acetate as the eluent and yielded 0.91 g (1.30 mmol, 39.2% of theory) of (3R,4R)-3-

[1-(2-acetylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a yellow oil; MS: 702 (M+H)$^+$.

(e) A solution of 0.88 g (1.25 mmol) of (3R,4R)-3-[1-(2-acetylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester in 9 ml of 1,2-dichloroethane was treated with 0.62 g (2.75 mmol, 2.2 equiv.) of anhydrous zinc bromide. The suspension was stirred for 2 h at 50° C. under Argon atmosphere. Subsequently, it was poured into a mixture of 100 ml of ice/water and 10 ml of sat. sodium bicarbonate solution. The aqueous phase was extracted five times with 50 ml of ethyl acetate. The combined organic phases were washed three times with 20 ml of water, dried over magnesium sulphate, evaporated under reduced pressure and dried in a high vacuum. The thus-obtained crude product was purified by chromatography on silica gel using a 100:10:1 v/v/v mixture of dichloromethane/methanol/28% ammonium hydroxide solution as the eluent and yielded 0.36 g (0.60 mmol, 48.0% of theory) of (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide as a light yellow oil; MS: 602 (M+H)$^+$.

Example 2

(a) In analogy to the procedure described in example 1(a) the (3RS,4RS)-3-hydroxy-4-(4-hydroxy-phenyl)-piperidin-1-carbonsäure tert-butyl ester (WO 97/09311) was treated with 1-(3-chloro-propoxymethyl)-2-methoxy-benzene (WO 97/09311) to the (3RS,4RS)-3-hydroxy-4-]4-[3-(2-methoxy-benzyloxy)-propoxy]-phenyl]-piperidine-1-carboxylic acid tert-butyl ester as a colorless solid; MS: 489 (M+NH$_4^+$)$^+$.

(b) In analogy to the procedure described in example 1(b) the (3RS,4RS)-3-hydroxy-4-[4-[3-(2-methoxy-benzyloxy)-propoxy]-phenyl]-piperidine-1-carboxylic acid tert-butyl ester was alkylated with 7-bromomethyl-quinoline hydrobromide (1:1) [J. Am. Chem. Soc. 77, 1054(1955)] to yield the (3RS,4RS)-4-[4-[3-(2-methoxy-benzyloxy)-propoxy]-phenyl]-3-(quinolin-7-ylmethoxy)-piperidine-1-carboxylic acid tert-butyl ester as an amorphous light yellow solid; MS: 613 (M+H)$^+$.

(c) In analogy to the procedure described in example 1(c) the (3RS,4RS)-4-[4-[3-(2-methoxy-benzyloxy)-propoxy]-phenyl]-3-(quinolin-7-ylmethoxy)-piperidine-1-carboxylic acid tert-butyl ester was reduced with sodium borohydride in presence of nickel(II) chloride hexahydrate to yield the (3RS,4RS)-4-[4-[3-(2-methoxy-benzyloxy)-propoxy]-phenyl]-3-(1,2,3,4-tetrahydro-quinolin-7-ylmethoxy)-piperidine-1-carbocylic acid tert-butyl ester as a light yellow oil; MS: 617 (M+H)$^+$.

(d) A solution of 0.67 g (1.09 mmol) of (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester in 10 ml of absolute N,N-dimethylformamide was successively treated at 0° C. with 0.21 g (1.30 mmol, 1.2 equiv.) of ethyl bromoacetate and 0.057 g (1.30 g, 1.30 mmol, 1.2 equiv.) of sodium hydride dispersion (55% in mineral oil). The mixture was then stirred for 2 h at 80° C. Then 0.047 g (1.09 mmol, 1.0 equiv.) of sodium hydride suspension (55% in mineral oil) and 0.18 g (1.09 mmol, 1.0 equiv.) of ethyl bromoacetate was added, and the suspension was stirred for another 8 h at 80° C. Subsequently, the suspension was poured into 100 ml of an ice/water mixture and extracted three times with 50 ml of ethyl acetate. The combined organic phases were washed three times with 20 ml of water, dried over magnesium sulphate, evaporated under reduced pressure and dried in a high vacuum. The thus-obtained crude product was purified by chromatography on silica gel using a 19:1 mixture of dichloromethane and ethyl acetate as the eluent and yielded 0.25 g (0.36 mmol, 33.0% of theory) of (3RS,4RS)-3-(1-ethoxycarbonylmethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester as a light yellow oil; MS: 703 (M+H)$^+$.

(e) In analogy to the procedure described in example 1(e), the (3RS,4RS)-3-(1-ethoxycarbonylmethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester was deprotected with zinc bromide in dichloroethane to yield the (3RS,4RS)-[7-(4-[4-[3-(2-methoxy-benzyloxy)-propoxy]-phenyl]-piperidin-3-yloxymethyl)-3,4-dihydro-2H-quinolin-1-yl]-acetic acid ethyl ester as a yellow oil; MS: 603 (M+H)$^+$.

Example 3

(a) In analogy to the procedure described in example 2(d) the (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 2(c)] was alkylated with iodoacetamide to yield the (3RS,4RS)-3-(1-carbamoyl-methyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester as a yellow oil; MS: 674 (M+H)$^+$.

(b) In analogy to the procedure described in example 1(e), the (3RS,4RS)-3-(1-carbamoylmethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester was deprotected with zinc bromide to yield the (3RS,4RS)-2-[7-[4-[4-[3-(2-methoxy-benzyloxy)-propoxy]-phenyl]-piperidin-3-yloxymethyl-3,4-dihydro-2H-quinolin-1-yl]-acetamide as a colorless oil; MS: 574 (M+H)$^+$.

Example 4

(a) A solution of 2.08 g (3.37 mmol) of (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 1(c)], and 1.41 g (10.14 mmol, 3.0 equiv.) of 3-bromo-1-propanol in 10 ml of toluene and 0.1 ml of N-methyl-pyrrolidone was treated with 1.44 g (10.14 mmol, 3.0 equiv.) of anhydrous disodium hydrogen phosphate. The suspension was refluxed for 24 h under an inert atmosphere. Subsequently, the reaction mixture was poured into 200 ml of an ice/water mixture and extracted three times with 150 ml of ethyl acetate. The combined organic phases were washed five times with 20 ml of water, dried over magnesium sulphate, evaporated under reduced pressure and dried in a high vacuum. The thus-obtained crude product was purified by chromatography on silica gel using a 1:1 mixture of hexane and ethyl acetate as the eluent and yielded 1.94 g (2.87 mmol, 85.2% of theory) of (3R,4R)-3-[1-(3-hydroxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a yellow oil; MS: 675 (M+H)$^+$.

(b) A solution of 0.200 g (0.296 mmol) (3R,4R)-3-[1-(3-hydroxy-propyl)-1,2,3,4-tetrahydro-quinolin-7-ylmethoxy]-4-[4-[3-(2-methoxy-benzyloxy)-propoxy]-phenyl]-phenyl]- piperidine-1-carboxylic acid tert-butyl ester in 1.5 ml methanol was treated with 1.5 ml of HCl 2N/methanol. The mixture was stirred for 6 h at 50° C. The reaction mixture was poured into a mixture of 100 ml of ice/water and 10 ml of sat. sodium bicarbonate solution. The aqueous phase was extracted five times with 50 ml of ethyl acetate. The combined organic phases were washed three times with 20 ml of water, dried over magnesium sulphate, evaporated under reduced pressure and dried in a high vacuum. The thus-obtained crude product was purified by chromatography on silica gel using a 100:10:1 v/v/v mixture of dichloromethane/methanol/28% ammonium hydroxide solution as the eluent and yielded 0.126 g (0.219 mmol, 74.1% of theory) of (3R,4R)-3-[1-(3-hydroxy-propyl)-1,2,3,4-tetrahydro-quinolin-7-ylmethoxy]-4-[4-[3-(2-methoxy-benzyloxy)-propoxy]-phenyl]-piperidine as a light yellow oil; MS: 575 (M+H)$^+$.

Example 5

(a) In analogy to the procedure described in example 4(a), the (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 1(c)] was alkylated with 2-bromo-1-ethanol to yield the (3R,4R)-3-[1-(2-hydroxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 661 (M+H)$^+$.

(b) In analogy to the procedure described in example 4(b), the (3R,4R)-3-[1-(2-hydroxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-2-[7-[4-[4-[3-(2-methoxy-benzyloxy)-propoxy]-phenyl]-piperidin-3-yloxymethyl]-3,4-dihydro-2H-quinolin-1-yl]-ethanol as a light yellow oil; MS: 561 (M+H)$^+$.

Example 6

(a) A solution of 0.133 g (0.189 mmol) of (3RS,4RS)-3-(1-ethoxycarbonylmethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester [example 2(d)] in 5 ml of methanol was treated with 0.10 g (0.72 mmol) of anhydrous potassium carbonate. The suspension was stirred for 1 h at 25° C. The salts were filtered off, the filtrate was concentrated. The thus-obtained crude product was purified by chromatography on silica gel using a 2:1 mixture of hexane and ethyl acetate as the eluent, and yielded 0.060 g (0.087 mmol, 46.1% of theory) of (3RS,4RS)-4-[4-[3-(2-methoxy-benzyloxy)-propoxy]-phenyl]-3-(1-methoxycarbonylmethyl-1,2,3,4-tetrahydro-quinolin-7-ylmethoxy)-piperidine-1-carboxylic acid tert-butyl ester as yellow oil; MS: 689 (M+H)$^+$.

(b) In analogy to the procedure described in example 1(e), the (3RS,4RS)-4-[4-[3-(2-methoxy-benzyloxy)-propoxy]-phenyl]-3-(1-methoxycarbonylmethyl-1,2,3,4-tetrahydro-qulinolin-7-ylmethoxy)-piperidine-1-carboxylic acid tert-butyl ester was deprotected with zinc bromide in dichloroethane to yield the (3RS,4RS)-[7-(4-[4-[3-(2-methoxy-benzyloxy)-propoxy]-phenyl]-piperidin-3-yloxymethyl]-3,4-dihydro-2H-quinolin-1-yl]-acetic acid methyl ester as a colorless oil; MS: 589 (M+H)$^+$.

Example 7

(a) In analogy to the procedure described in example 4(a), the (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 2(c)] was alkylated with methyl-3-bromopropanoate to yield the (4RS,5RS)-4-[4-[3-(2-methoxy-benzyloxy)-propoxy]-phenyl]-3-[1-(2-methoxycarbonyl-ethyl)-1,2,3,4-tetrahydro-quinolin-7-ylmethoxy]-piperidine-1-carboxylic acid tert-butyl ester as a colorless oil; MS: 703 (M+H)$^+$.

(b) In analogy to the procedure described in example 1(e), the (4RS,5RS)-4-[4-[3-(2-methoxy-benzyloxy)-propoxy]-phenyl]-3-[1-(2-methoxycarbonyl-ethyl)-1,2,3,4-tetrahydro-quinolin-7-ylmethoxy]-piperidine-1-carboxylic acid tert-butyl ester was deprotected to yield the (3RS,4RS)-3-[7-(4-[4-[3-(2-methoxy-benzyloxy)-propoxy]-phenyl]-piperidin-3-yloxymethyl)-3,4-dihydro-2H-quinolin-1-yl]-propionic acid methyl ester as a colorless oil; MS: 603(M+H)$^+$.

Example 8

(a) Following exactly the procedure described in example 4(a), the (3RS,4RS)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 2(c)] was alkylated with 3-bromo-1-propanol to yield the (4RS,5RS)-3-[1-(3-hydroxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a colorless oil; MS: 675 (M+H)$^+$.

(b) To an ice-cooled solution of 0.040 g (0.059 mmol) of (4RS,5RS)-3-[1-(3-hydroxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester and 0.078 g (0.077 mmol, 1.3 equiv.) triethylamine in 2 ml of dichloromethane was added dropwise 0.074 g (0.065 mmol, 1.1 equiv.) of methanesulfonyl chloride. The reaction mixture was then stirred for 1 h at 0° C., 1 h at room temperature, poured into 100 ml of an ice/water mixture and extracted three times with 50 ml of ethyl acetate. The combined organic phases were washed three times with 20 ml of water, dried over magnesium sulphate, evaporated under reduced pressure and dried in a high vacuum. The thus-obtained crude product was purified by chromatography on silica gel using a 2:1 mixture of hexane and ethyl acetate as the eluent and yielded 0.029 g (0.039 mmol, 66.1% of theory) of (4RS,5RS)-3-[1-(3-methanesulfonyloxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 753 (M+H)$^+$.

(c) 0.029 g (0.039 mmol) (4RS,5RS)-3-[1-(3-methanesulfonyloxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester were dissolved in 1 ml of a 33% solution of methylamine in ethanol. After 5 h stirring at 25° C., the reaction mixture was poured into 25 ml of an ice/water mixture and extracted three times with 25 ml of dichloromethane. The combined organic phases were washed twice with 20 ml of water, evaporated under reduced pressure, and dried in a high vacuum. The thus-obtained crude product was purified by chromatography on silica gel using a 100:10:1 v/v/v mixture of dichloromethane/methanol/28% ammonium hydroxide solution as the eluent to yield 0.019 g (0.028 mmol, 71.8% of theory) of (3RS,4RS)-4-[4-[3-(2-methoxy-benzyloxy)-propoxy]-phenyl]-3-[1-(3-methylamino-propyl)-1,2,3,4-tetrahydro-quinolin-7-ylmethoxy]-piperidine-1-carboxylic acid tert-butyl ester as a yellow oil; MS: 688 (M+H)$^+$.

(d) In analogy to the procedure described in example 4(b), the (3RS,4RS)-4-[4-[3-(2-methoxy-benzyloxy)-propoxy]-phenyl]-3-[1-(3-methylamino-propyl)-1,2,3,4-tetrahydro-quinolin-7-ylmethoxy]-piperidine-1-carboxylic acid tert-butyl ester was deprotected with HCl/methanol to yield the (3RS,4RS)-[3-[7-[4-[4-[3-(2-methoxy-benzyloxy)-propoxyl]-phenyl]-piperidin-3-yloxymethyl]-3,4-dihydro-2H-quinolin-1-yl]-propyl]-methyl-amine as a light yellow oil; MS: 588 (M+H)$^+$.

Example 9

(a) In analogy to the procedure described in example 8(b), the (3R,4R)-3-[1-(2-hydroxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 5(a)] was treated with methanesulfonyl chloride to yield the (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a yellow oil; MS: 739 (M+H)$^+$.

(b) In analogy to the procedure described in example 8(c), the (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was treated with methylamine to yield the (3R,4R)-4-[4-[3-(2-methoxy-benzyloxy)-propoxy]-phenyl]-3-[1-(2-methylamino-ethyl)-1,2,3,4-tetrahydro-quinolin-7-ylmethoxy]-piperidine-1-carboxylic acid tert-butyl ester as a yellow oil; MS: 674 (M+H)$^+$.

(c) In analogy to the procedure described in example 4(b), the (3R,4R)-4-[4-[3-(2-methoxy-benzyloxy)-propoxy]-phenyl]-3-[1-(2-methylamino-ethyl)-1,2,3,4-tetrahydro-quinolin-7-ylmethoxy]-piperidine-1-carboxylic acid tert-butyl ester was deprotected with HCl/methanol to yield the (3R,4R)-[2-[7-[4-[4-[3-(2-methoxy-benzyloxy)-propoxy]-phenyl]-piperidin-3-yloxymethyl]-3,4-dihydro-2H-quinolin-1-yl]-ethyl]-methyl-amine as a yellow oil; MS: 574 (M+H)$^+$.

Example 10

(a) In analogy to the procedure described in example 8(b), the (3R,4R)-3-[1-(3-hydroxy-propoyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 4(a)] was treated with methanesulfonyl chloride to yield the (3R,4R)-3-[1-(3-methanesulfonyloxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester, which was directly used in the next step without further characterization.

(b) A solution of 0.200 g (0.266 mmol) of crude (3R,4R)-3-[1-(3-methanesulfonyloxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester in 1.8 ml of absolute N,N-dimethylformamide was treated with 0.025 g (0.398 mmol, 1.5 equiv.) of anhydrous sodium azide, and stirred for 45 min. at 50° C. The reaction mixture was then poured into 50 ml of an ice/water mixture and extracted three times with 50 ml of ethyl acetate. The combined organic phases were washed twice with 20 ml of water, evaporated under reduced pressure and dried in a high vacuum. The thus-obtained crude product was purified by chromatography on silica gel using a 3:1 mixture of hexane and ethyl acetate as the eluent and yielded 0.162 g (0.231 mmol, 86.8% of theory) of (3R,4R)-3-[1-(3-azido-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 700 (M+H)$^+$.

(c) 0.026 g (0.695 mmol, 3.0 equiv.) of sodium borohydride was added in four portions to a well stirred solution of 0.162 g (0.231 mmol) (3R,4R)-3-[1-(3-azido-propyl)-1,2,3,4-tetrahydro-qulinolin-7-ylmethoxy]-4-[4-[3-(2-methoxy-benzyloxy,)-propoxy]-phenyl]-piperidine-1-carboxylic acid tert-butyl ester and 0.028 g (0.116 mmol, 0.5 equiv.) of nickel(II) chloride hexahydrate in 1.5 ml of methanol. After stirring for 15 min at 25° C., the reaction mixture was poured into a well stirred mixture of 50 ml of ice-water and 10 ml sat. ammonium chloride solution, and stirred for 15 min. The light blue aqueous phase was extracted three times with 50 ml of ethyl acetate. The combined organic phases were washed twice with 20 ml of water, evaporated under reduced pressure and dried in a high vacuum. The thus-obtained crude product was purified by chromatography on silica gel using a 140:10:1 v/v/v mixture of dichloromethane/methanol/28% ammonium hydroxide solution as the eluent to yield 0.120 g (0.178 mmol, 77.1% of theory) of (3R,4R)-3-[1-(3-amino-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 674 (M+H)$^+$.

(d) In analogy to the procedure described in example 4(b), the (3R,4R)-3-[1-(3-amino-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-3-[7-(4-[4-[3-(2-methoxy-benzyloxy)-propoxy]-phenyl]-piperidin-3-yloxymethyl)-3,4-dihydro-2H-quinolin-1-yl]-propylamine as yellow oil; MS: 574 (M+H)$^+$.

Example 11

(a) To an ice-cooled solution of 0.070 g (0.104 mmol) of (3R,4R)-3-[1-(3-amino-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 10(c)] and 0.013 g (0.125 mmol, 1.2 equiv.) of triethylamine in 1 ml of dichloromethane was added dropwise 0.009 g (0.114 mmol, 1.1 eqiuv.) of acetyl chloride. The reaction was allowed to warm to room temperature, poured into 50 ml of an ice/water mixture and extracted three times with 50 ml of ethyl acetate. The combined organic phases were washed twice with 20 ml of water, evaporated under reduced pressure and dried in a high vacuum. The thus-obtained crude product was purified by chromatography on silica gel using ethyl acetate as the eluent and yielded 0.068 g (0.095 mmol, 91.3% of theory) of (3R,4R)-3-[1-(3-acetylamino-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 716 (M+H)$^+$.

(b) In analogy to the procedure described in example 1(e), the (3R,4R)-3-[1-(3-acetylamino-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with zinc bromide to yield the (3R,4R)-N-[3-[7-(4-[4-[3-(2-methoxy-benzyloxy)-propoxy]-phenyl]-piperidin-3-yloxymethyl)-3,4-dihydro-2H-quinolin-1-yl]-propyl]-acetamide as a light yellow oil; MS: 616 (M+H)$^+$.

Example 12

(a) To a well stirred solution of 0.200 g (0.266 mmol) of crude (3R,4R)-3-[1-(3-methanesulfonyloxy-propyl)-1,2,3, 4-tetrahydro-quinolin-7-ylmethoxy]-4-[4-[3-(2-methoxy-benzyloxy)-propoxy]-phenyl]-piperidine-1-carboxylic acid tert-butyl ester [example 10(a)] in 1.8 ml of absolute N,N-dimethylformamide was added 0.026 (0.399 mmol, 1.5 equiv.) of potassium cyanide. After stirring for 45 min at 50° C., the reaction was allowed to warm to room temperature, poured into 50 ml of an ice/water mixture and extracted three times with 50 ml of ethyl acetate. The combined organic phases were washed twice with 20 ml of water, evaporated under reduced pressure and dried in a high vacuum. The thus-obtained crude product was purified by chromatography on silica gel using a 2:1 mixture of hexane and ethyl acetate as the eluent to yield 0.130 g (0.190 mmol, 71.4% of theory) of (3R,4R)-3-[1-(3-cyano-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 684 (M+H)+.

(b) To a well stirred solution of 0.130 g (0.190 mmol) of (3R,4R)-3-[1-(3-cyano-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester in 0.5 ml of absolute THF was added dropwise 1 ml of a 1M solution of borane-THF complex in THF. After stirring for 3 h at 70° C., the reaction was allowed to warm to room temperature, poured into 50 ml of an ice/water mixture and extracted three times with 50 ml of ethyl acetate. The combined organic phases were washed twice with 20 ml of water, evaporated under reduced pressure and dried in a high vacuum. The thus-obtained crude product was purified by chromatography on silica gel using a 140:10:1 v/v/v mixture of dichloromethane/methanol/28% ammonium hydroxide solution as the eluent to yield 0.090 g (0.131 mmol, 68.9% of theory) of (3R,4R)-3-[1-(4-amino-butyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 688 (M+H)+.

(c) In analogy to the procedure described in example 4(b), the (3R,4R)-3-[1-(4-amino-butyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-4-[7-(4-[4-[3-(2-methoxy-benzyloxy)-propoxy]-phenyl]-piperidin-3-yloxymethyl)-3,4-dihydro-2H-quinolin-1-yl]-butylamine as a light yellow oil; MS: 588 (M+H)+.

Example 13

(a) A solution of 0.220 g (0.298 mmol) (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 9(a)] and 0.30 g (0.446 mmol, 1.50 equiv.) of imidazole in 1.8 ml of absolute N,N-dimethylformamide was stirred for 4 h at 80° C. The reaction was allowed to warm to room temperature, poured into 50 ml of an ice/water mixture and extracted three times with 50 ml of diethyl ether. The combined organic phases were washed twice with 20 ml of water, evaporated under reduced pressure and dried in a high vacuum. The thus obtained crude product was purified by chromatography on silica gel using a 20:1 v/v mixture of dichloromethane/methanol as the eluent to yield 0.067 g (0.094 mmol, 31.5% of theory) of (3R,4R)-3-[1-(2-imidazol-1-yl-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 711 (M+H)+.

(b) In analogy to the procedure described in example 4(b), the (3R,4R)-3-[1-(2-imidazol-1-yl-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-1-(2-imidazol-1-yl-ethyl)-7-(4-[4-[3-(2-methoxy-benzyloxy)-propoxy]-phenyl]-piperidin-3-yloxymethyl)-1,2,3,4-tetrahydro-quinoline as a yellow oil; MS: 611 (M+H)+.

Example 14

(a) To an ice cooled solution of 0.240 g (0.319 mmol) of crude (3R,4R)-3-[1-(3-methanesulfonyloxy-propyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 10(a)] in 3 ml of absolute methanol was added 0.0 17 g (0.383, 1.2 equiv.) of sodium hydride (55% suspension in mineral oil). The reaction was then stirred for 6 h at 50° C., allowed to cool to room temperature, poured into 50 ml of an ice/water mixture and extracted three times with 50 ml of ethyl acetate. The combined organic phases were washed twice with 20 ml of water, evaporated under reduced pressure and dried in a high vacuum. The thus obtained crude product was purified by chromatography on silica gel using a 2:1 v/v mixture of hexane and ethyl acetate as eluent to yield 0.143 g (0.208 mmol, 65.2% of theory) of (3R,4R)-4-[4-[3-(2-methoxy-benzyloxy)-propoxy]-phenyl]-3-[1-(3-methoxy-propyl)-1,2,3,4-tetrahydro-quinolin-7-ylmethoxy]-piperidine-1-carboxylic acid tert-butyl ester as a yellow oil; MS: 689 (M+H)+.

(b) In analogy to the procedure described in example 4(b), the (3R,4R)-4-[4-[3-(2-methoxy-benzyloxy)-propoxy]-phenyl]-3-[1-(3-methoxy-propyl)-1,2,3,4-tetrahydro-quinolin-7-ylmethoxy]-piperidine-1-carboxylic acid tert-butyl ester was deprotected with HCl/methanol to yield the (3R,4R)-4-[4-[3-(2-methoxy-benzyloxy)-propoxy]-phenyl]-3-[1-(3-methoxy-propyl)-1,2,3,4-tetrahydro-quinolin-7-ylmethoxy]-piperidine as a yellow oil; MS: 589 (M+H)+.

Example 15

(a) In analogy to the procedure described in example 10(b), the (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 9(a)] was treated with sodium azide to yield the (3R,4R)-3-[1-(2-azido-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 686 (M+H)+.

(b) In analogy to the procedure described in example 10(c), the (3R,4R)-3-[1-(2-azido-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was reduced with sodium borohydride in presence of nickel(II) chloride hexahydrate to yield the (3R,4R)-3-[1-(2-amino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 660 (M+H)+.

(c) In analogy to the procedure described in example 4(b), the (3R,4R)-3-[1-(2-amino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R )-2-[7-[4-[4-[3-(2-methoxy-benzyloxy)-propoxy]-phenyl]-piperidin-3-yloxymethyl]-3,4-dihydro-2H-quinolin-1-yl]-ethylamine as a light yellow oil; MS: 560 (M+H)+.

Example 16

(a) A solution of 2.50 g (4.05 mmol) of (3R,4R)-4-[4-[3-(2-methoxy-benzyloxy)-propoxy]-phenyl]-3-(1,2,3,4-tetrahydro-quinolin-7-ylmethoxy)-piperidine-1-carboxylic acid tert-butyl ester [example 1(c)] and 0.968 g (8.10 mmol, 2.0 equiv.) of bromoacetonitrile in 15 ml of toluene and 2 ml of N-methyl pyrrolidone was treated with 2.88 g (20.27 mmol, 5.0 equiv.) of anhydrous disodium hydrogen phosphate. The suspension was stirred for 18 h at 50° C., allowed to cool to room temperature, poured into 100 ml of an ice/water mixture and extracted three times with 200 ml of ethyl acetate. The combined organic phases were washed twice with 50 ml of water, evaporated under reduced pressure and dried in a high vacuum. The thus obtained crude product was purified by chromatography on silica gel using a 10:1 v/v mixture of dichloromethane and ethyl acetate as eluent to yield 2.28 g (3.48 mmol, 85.9% of theory) of (3R,4R)-3-(1-cyanomethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester as a light yellow oil; MS: 656 $(M+H)^+$.

(b) In analogy to the procedure described in example 4(b), the (3R,4R)-3-(1-cyanomethyl-1,2,3,4-tetrahydro-quinolin-7-ylmethoxy)-4-[4-[3-(2-methoxy-benzyloxy)-propoxy]-phenyl]-piperidine-1-carboxylic acid tert-butyl ester was deprotected with HCl/methanol to yield the (3R,4R)-[7-(4-[4-[3-(2-methoxy-benzyloxy)-propoxy]-phenyl]-piperidin-3-yloxymethyl)-3,4-dihydro-2H-quinolin-1-yl]-acetonitrile as a yellow oil; MS: 556 $(M+H)^+$.

Example 17

(a) In analogy to the procedure described in example 14(a), the (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 9(a)] was treated with methanol/sodium hydride to yield the (3R,4R)-4-[4-[3-(2-methoxy-benzyloxy)-propoxy]-phenyl]-3-[1-(2-methoxy-ethyl)-1,2,3,4-tetrahydro-quinolin-7-ylmethoxy]-piperidine-1-carboxylic acid tert-butyl ester as a light yellow oil; MS: 675 $(M+H)^+$.

(b) In analogy to the procedure described in example 4(b), the (3R,4R)-4-[4-[3-(2-methoxy-benzyloxy)-propoxy]-phenyl]-3-[1-(2-methoxy-ethyl)-1,2,3,4-tetrahydro-quinolin-7-ylmethoxy]-piperidine-1-carboxylic acid tert-butyl ester was deprotected with HCl/methanol to yield the (3R,4R)-7-[4-[4-[3-(2-methoxy-benzyloxy)-propoxy]-phenyl]-piperidin-3-yloxymethyl]-1-(2-methoxy-ethyl)-1,2,3,4-tetrahydro-quinoline as a light yellow oil; MS: 575 $(M+H)^+$.

Example 18

(a) To an ice-cooled solution of 0.250 g (0.379 mmol) (3R,4R)-3-[1-(2-amino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 15(b)] and 0.049 g (0.493 mmol, 1.3 equiv.) triethylamine in 5 ml of dichloromethane was added dropwise at 0° C. 0.047 g (0.417 mmol, 1.1 equiv.) methanesulfonyl chloride. After stirring for 30 min at 0° C., the reaction mixture was poured into 50 ml of an ice/water mixture and extracted three times with 50 ml of ethyl acetate. The combined organic phases were washed twice with 25 ml of water, evaporated under reduced pressure and dried in a high vacuum. The thus obtained crude product was purified by chromatography on silica gel using a 1:2 v/v mixture of hexane and ethyl acetate as eluent to yield 0.247 g (0.335 mmol, 88.3% of theory) of (3R,4R)-3-[1-(2-methanesulfonylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 736 $(M+H)^+$.

(b) In analogy to the procedure described in example 4(b), the (3R,4R)-3-[1-(2-methanesulfonylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-3-[1-(2-methanesulfonylamino-ethyl)-1,2,3,4-tetrahydro-quinolin-7-ylmethoxy]-4-[4-[3-(2-methoxy-benzyloxy)-propoxy]-phenyl]-piperidine as a light yellow oil; MS: 638 $(M+H)^+$.

Example 19

(a) A solution of 0.100 g (0.152 mmol) (3R,4R)-3-[1-(2-amino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 15(b)] and 0.029 g (0.303 mmol, 2.0 equiv.) of sulfamide in 3 ml of tetrahydrofuran was refluxed for 72 h. The reaction mixture was poured into 50 ml of an ice/water mixture and extracted three times with 50 ml of ethyl acetate. The combined organic phases were washed twice with 25 ml of water, evaporated under reduced pressure and dried in a high vacuum. The thus obtained crude product was purified by chromatography on silica gel using a 100:10:1 v/v/v mixture of dichloromethane/methanol/28% ammonium hydroxide solution as eluent to yield 0.071 g (0.096 mmol, 63.2% of theory) of (3R,4R)-3-[1-(2-sulfamoylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a yellow oil; MS: 739 $(M+H)^+$.

(b) In analogy to the procedure described in example 1(e), the (3R,4R)-3-[1-(2-sulfamoylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with zinc bromide in 1,2-dichloroethane to yield the (3R,4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-sulfamide as a yellow oil; MS: 639 $(M+H)^+$.

Example 20

(a) In analogy to the procedure described in example 8(c), the (3R,4R)-3-[1-(2-methanesulfonyloxy-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester [example 9(a)] was treated with dimethylamine in ethanol to yield the (3R,4R)-3-[1-(2-dimethylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester as a light yellow oil; MS: 688 $(M+H)^+$.

(b) In analogy to the procedure described in example 4(b), the (3R,4R)-3-[1-(2-dimethylamino-ethyl)-1,2,3,4-tetrahydro-quinolin-7-ylmethoxy]-4-[4-[3-(2-methoxy-benzyloxy)-propoxy]-phenyl]-piperidine-1-carboxylic acid tert-butyl ester was deprotected with HCl/methanol to yield the (3R,4R)-[2-[7-(4-[4-[3-(2-methoxy-benzyloxy)-propoxy]-phenyl]-piperidin-3-yloxymethyl)-3,4-dihydro-2H-quinolin-1-yl]-ethyl]-dimethyl-amine as a yellow oil; MS: 588 $(M+H)^+$.

Example 21

(a) To a solution of 0.103 g (0.156 mmol) (3R,4R)-3-[1-(2-amino-ethyl)-1,2,3,4-tetrahydro -quinolin-7-ylmethoxy]-4-[4-[3-(2-methoxy-benzyloxy)-propoxy]-phenyl]-piperidine-1-carboxylic acid tert-butyl ester [example 15(b)] in 2 ml of tetrahydrofuran was added a solution of 0.101 g (1.56 mmol, 10.0 equiv.) of sodium cyanate in 1 ml of water. The resulting suspension was cooled to 0° C. and 0.156 ml (0.156 mmol, 1.0 equiv.) of 1 N HCl solution was added dropwise. The reaction flask was stoppered and the suspension was stirred for 2 h at 25° C. The reaction mixture was poured into 50 ml of an ice/water mixture, the pH was adjusted to 8 by addition of saturated sodium bicarbonate solution, and the aqueous phase was extracted three times with 50 ml of ethyl acetate. The combined organic phases were washed twice with 25 ml of water, evaporated under reduced pressure and dried in a high vacuum. The thus obtained crude product was purified by chromatography on silica gel using a 100:10:1 v/v/v mixture of dichloromethane/methanol/28% ammonium hydroxide solution as eluent to yield 0.106 g (0.133 mmol, 85.3% of theory) of (3R,4R)-4-[4-[3-(2-methoxy-benzyloxy)-propoxy]-phenyl]-3-[1-(2-ureido-ethyl)-1,2,3,4-tetrahydro-quinolin-7-ylmethoxy]-piperidine-1-carboxylic acid tert-butyl ester as a yellow oil; MS: 799 (M+H)$^+$.

(b) In analogy to the procedure described in example 4(b), the (3R,4R)-4-[4-[3-(2-methoxy-benzyloxy)-propoxy]-phenyl]-3-[1-(2-ureido-ethyl)-1,2,3,4-tetrahydro-quinolin-7-ylmethoxy]-piperidine-1-carboxylic acid tert-butyl ester was deprotected with HCl/methanol to yield the (3R,4R)-[[2-[7-[4-[4-[3-(2-methoxy-benzyloxy)-propoxy]-phenyl]-piperidin-3-yloxymethyl]-3,4-dihydro-2H-quinolin-1-yl]-ethyl]-urea as yellow oil; MS: 603 (M+H)$^+$.

Example 22

(a) In analogy to the procedure described in example 11(a) the (3R,4R)-3-[1-(2-amino-ethyl)-1,2,3,4-tetrahydro-qulinolin-7-ylmethoxy]-4-[4-[3-(2-methoxy-benzyloxy)-propoxy]-phenyl]-piperidine-1-carboxylic acid tert-butyl ester [example 15(b)] was acylated with trifluoroacetyl chloride to yield the (3R,4R)-4-[4-[3-(2-methoxy-benzyloxy)-propoxy]-phenyl]-3-[1-[2-(2,2,2-trifluoro-acetylamino)-ethyl]-1,2,3,4-tetrahydro-quinolin-7-ylmethoxy]-piperidine-1-carboxylic acid tert-butyl ester as a yellow oil; MS: 756 (M+H)$^+$.

(b) In analogy to the procedure described in example 1(e), the (3R,4R)-4-[4-[3-(2-methoxy-benzyloxy)-propoxy]-phenyl]-3-[1-[2-(2,2,2-trifluoro-acetylamino)-ethyl]-1,2,3,4-tetrahydro-quinolin-7-ylmethoxyl-piperidine-1-carboxylic acid tert-butyl ester was deprotected with zinc bromide in 1,2-dichloroethane to yield the (3R,4R)-2,2,2-trifluoro-N-[2-[7-[4-[4-[3-(2-methoxy-benzyloxy)-propoxy]-phenyl]-piperidin-3-yloxymethyl]-3,4-dihydro-2H-quinolin-1-yl]-acetamide as a yellow oil; MS: 656 (M+H)$^+$.

Example 23

(a) In analogy to the procedure described in example 1(a), the (3R,4R)-3-hydroxy-4-(4-hydroxy-phenyl)-piperidine-1-carboxylic acid tert-butyl was reacted with rac-2-(3-bromopropoxy)tetrahydro-2H-pyran [J.Org.Chem. 53, (1988), 25, 5903–5908] and potassium carbonate in N,N-dimethylformamide to yield an 1:1 mixture of the (3R,4R)-3-hydroxy-4-[4-[3-[(R)- and (S)-tetrahydro-pyran-2-yloxy]-propoxy]-phenyl]-piperidine-1-carboxylic acid tert-butyl esters as a colorless oil; MS: 435 (M+H)$^+$.

(b) In analogy to the procedure described in example 1(b), the 1:1 mixture of the (3R,4R)-3-hydroxy-4-[4-[3-[(R)- and (S)-tetrahydro-pyran-2-yloxy]-propoxy]-phenyl]-piperidine-1-carboxylic acid tert-butyl esters was reacted with 7-bromomethyl-quinoline hydrobromide (1:1) [J. Am. Chem. Soc. 77, 1054(1955)] in N,N-dimethylformamide in the presence of sodium hydride suspension to yield the mixture of the (3R,4R)-3-(quinolin-7-ylmethoxy)-4-[4-[3-[(R)- and (S)-tetrahydro-pyran-2-yloxy]-propoxy]-phenyl]-piperidine-1-carboxylic acid tert-butyl esters as a light yellow oil; MS: 577 (M+H)$^+$.

(c) To an ice-cooled solution of 8.74 g (15.15 mmol) of the mixture of the (3R,4R)-3-(quinolin-7-ylmethoxy)-4-[4-[3-[(R)- and -[(S)-tetrahydro-pyran-2-yloxy]-propoxy]-phenyl]-piperidine-1-carboxylic acid tert-butyl esters in 25 ml of methanol was added 25 ml of HCl 2N/methanol. The mixture was then warmed to room temperature and stirred for 1 h. The reaction mixture was poured into 200 ml of an ice/water mixture, the pH was adjusted to 8 by addition of saturated sodium bicarbonate solution, and the aqueous phase was extracted four times with 200 ml of ethyl acetate. The combined organic phases were washed twice with 25 ml of water, evaporated under reduced pressure and dried in a high vacuum. The thus obtained crude product was purified by cristallisation from ether to yield 5.40 g (10.96 mmol, 72.3% of theory) of the (3R,4R)-4-[4-(3-hydroxy-propoxy)-phenyl]-3-(quinolin-7-ylmethoxy)-piperidine-1-carboxylic acid tert-butyl ester as a white solid; MS: 493 (M+H)$^+$.

(d) In analogy to the procedure described in example 8(b), the (3R,4R)-4-[4-(3-hydroxy -propoxy)-phenyl]-3-(quinolin-7-ylmethoxy)-piperidine-1-carboxylic acid tert-butyl ester was reacted with methanesulfonyl chloride to yield the (3R,4R)-4-[4-(3-methanesulfonyloxy-propoxy)-phenyl]-3-(quinolin-7-ylmethoxy)-piperidine-1-carboxylic acid tert-butyl ester as a colorless solid; MS: 571 (M+H)$^+$.

(e) To an ice-cooled solution of 3.50 g (6.13 mmol) of the (3R,4R)-4-[4-(3-methanesulfonyloxy-propoxy)-phenyl]-3-(quinolin-7-ylmethoxy)-piperidine-1-carboxylic acid tert-butyl ester and 4.97 ml (4.42 g, 61.33 mmol, 10.0 equiv.) of cyclopropyl carbinol in 25 ml of tetrahydrofuran was added 0.535 g (12.27 mmol, 2.0 equiv.) of sodium hydride dispersion (55% in mineral oil) in portions. The mixture was warmed to 55° C. and stirred for 1.5 h. The reaction mixture was poured into 200 ml of an ice/water mixture, the pH was adjusted to 8 by addition of saturated sodium bicarbonate solution, and the aqueous phase was extracted four times with 200 ml of ethyl acetate. The combined organic phases were washed twice with 25 ml of water, evaporated under reduced pressure and dried in a high vacuum. The thus obtained crude product was purified by chromatography on silica gel using a 1:2 v/v mixture of hexane and ethyl acetate as eluent to yield 3.32 g (6.07 mmol, 99.0% of theory) of the (3R,4R)-4-[4-(3-cyclopropylmethoxy-propoxy)-phenyl]-3-(quinolin-7-ylmethoxy)-piperidine-1-carboxylic acid tert-butyl ester as a colorless oil; MS: 547 (M+H)$^+$.

(f) In analogy to the procedure described in example 1(c), the (3R,4R)-4-[4-(3-cyclopropylmethoxy-propoxy)-phenyl]-3-(quinolin-7-ylmethoxy)-piperidine-1-carboxylic acid tert-butyl ester was reduced with sodium borohydride in presence of Ni(II) chloride hexahydrate to yield the (3R, 4R)-4-[4-(3-cyclopropylmethoxy-propoxy)-phenyl]-3-(1,2,3,4-tetrahydro-quinolin-7-ylmethoxy)-piperidine-1-carboxylic acid tert-butyl ester as a light yellow oil; MS: 551 (M+H)$^+$.

(g) In analogy to the procedure described in example 4(a), the (3R,4R)-4-[4-(3-cyclopropylmethoxy-propoxy)- phenyl]-3-(1,2,3,4-tetrahydro-quinolin-7-ylmethoxy)-piperidine-1-carboxylic acid tert-butyl ester was reacted with 1-bromo-3-hydroxy-propane to yield the (3R,4R)-4-[4-(3-cyclopropylmethoxy-propoxy)-phenyl]-3-[1-(3-hydroxy-propyl)- 1,2,3,4-tetrahydro-quinolin-7-ylmethoxy]-piperidine-1-carboxylic acid tert-butyl ester as a light yellow oil; MS: 609 (M+H)$^+$.

(h) In analogy to the procedure described in example 8(b), the (3R,4R)-4-[4-(3-cyclopropylmethoxy-propoxy)-phenyl]-3-[1-(3-hydroxy-propyl)-1,2,3,4-tetrahydro-quinolin-7-ylmethoxy]-piperidine-1-carboxylic acid tert-butyl ester was reacted with methanesulfonyl chloride to yield the crude (3R,4R)-4-[4-(3-cyclopropylmethoxy-propoxy)-phenyl]-3-[1-(3-methanesulfonyloxy-propyl)-1,2,3,4-tetrahydro-quinolin-7-ylmethoxy]-piperidine-1-carboxylic acid tert-butyl ester which was used without further purification or characterization.

(i) In analogy to the procedure described in example 14(a), the crude (3R,4R)-4-[4-(3-cyclopropylmethoxy-propoxy)-phenyl]-3-1-(3-methanesulfonyloxy-propyl)-1,2,3,4-tetrahydro-quinolin-7-ylmethoxy]-piperidine-1-carboxylic acid tert-butyl ester was treated with sodium hydride/methanol to yield the (3R,4R)-4-[4-(3-cyclopropylmethoxy-propoxy)-phenyl]-3-]1-(3-methoxy-propyl)-1,2,3,4-tetrahydro-quinolin-7-ylmethoxy]-piperidine-1-carboxylic acid tert-butyl ester as a yellow oil; MS: 623 (M+H)$^+$.

(j) In analogy to the procedure described in example 4(b), the (3R,4R)-4-[4-(3-cyclopropylmethoxy-propoxy)-phenyl]-3-[1-(3-methoxy-propyl)-1,2,3,4-tetrahydro-quinolin-7-ylmethoxy]-piperidine-1-carboxylic acid tert-butyl ester was deprotected with HCl/methanol to yield the (3R,4R)-7-[4-[4-(3-cyclopropylmethoxy-propoxy)-phenyl]-piperidin-3-yloxymethyl]-1-(3-methoxy-propyl)-1,2,3,4-tetrahydro-quinoline as light yellow oil; MS: 523 (M+H)$^+$.

Example 24

(a) In analogy to the procedure described in example 23(e), the (3R,4R)-4-[4-(3-methanesulfonyloxy-propoxy)-phenyl]-3-(quinolin-7-ylmethoxy)-piperidine-1-carboxylic acid tert-butyl ester [example 23(d)] was reacted with 2,2,2-trifluoro-ethanol and sodium hydride suspension in tetrahydrofuran to yield the (3R,4R)-3-(quinolin-7-ylmethoxy)-4-[4-[3-(2,2,2-trifluoro-ethoxy)-propoxy]-phenyl]-piperidine-1-carboxylic acid tert-butyl ester as light yellow oil; MS: 575 (M+H)$^+$.

(b) In analogy to the procedure described in example 1(c), the (3R,4R)-3-(quinolin-7-ylmethoxy)-4-[4-[3-(2,2,2-trifluoro-ethoxy)-propoxy]-phenyl]-piperidine-1-carboxylic acid tert-butyl ester was reduced to yield the (3R,4R)-3-(1,2,3,4-tetrahydro-quinolin-7-ylmethoxy)-4-[4-[3-(2,2,2-trifluoro-ethoxy)-propoxy]-phenyl]-piperidine-1-carboxylic acid tert-butyl ester as a light yellow oil; MS: 579 (M+H)$^+$.

(c) In analogy to the procedure described in example 4(a), the (3R,4R)-3-(1,2,3,4-tetrahydro-quinolin-7-ylmethoxy)-4-[4-[3-(2,2,2-trifluoro-ethoxy)-propoxy]-phenyl]-piperidine-1-carboxylic acid tert-butyl ester was alkylated with 1-bromo-3-hydroxy-propane to yield the (3R,4R)-3-[1-(3-hydroxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester as a light yellow oil; MS: 637 (M+H)$^+$.

(d) In analogy to the procedure described in example 8(b), the (3R,4R)-3-[1-(3-hydroxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester was reacted with methanesulfonyl chloride to yield the (3R,4R)-3-[1-(3-methanesulfonyloxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester which was used without further purification or characterization.

(e) In analogy to the procedure described in example 14(a), the crude (3R,4R)-3-[1-(3-methanesulfonyloxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester was treated with sodium hydride/methanol to yield the (3R,4R)-3-[1-(3-methoxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester as a light yellow oil; MS: 651 (M+H)$^+$.

(f) In analogy to the procedure described in example 1(e), the (3R,4R)-3-[1-(3-methoxy-propyl)-1,2,3,4-tetrahydro-quinolin-7-ylmethoxy]-4-[4-[3-(2,2,2-trifluoro-ethoxy)-propoxy]-phenyl]-piperidine-1-carboxylic acid tert-butyl ester was deprotected to yield the (3R,4R)-3-[1-(3-methoxy-propyl)-1,2,3,4-tetrahydro-quinolin-7-ylmethoxy]-4-[4-[3-(2,2,2-trifluoro-ethoxy)-propoxy]-phenyl]-piperidine as a yellow oil; MS: 551 (M+H)$^+$.

Example A: Capsules

| Composition: | | |
|---|---|---|
| 1) | Compound of formula I, e.g., (3R,4R)-N-[2-[7-[4-[4-[3-(2-Methoxy-benzyloxy)-propoxy]-phenyl]-piperidin-3-yloxymethyl]-3,4-dihydro-2H-quinolin-1-yl]-ethyl]-acetamide | 50 mg |
| 2) | Medium-chain mono-, diglyceride | 950 mg |

Production 2) is liquefied by gentle heating and 1) is dissolved in 2). The mixture is filled into hard or soft gelatine capsules of suitable size. The hard gelatine capsules may be sealed, for example using the Quali-Seal technique.

Example B: Injection Solution in Form of a Mixed Micelle Solution

| Composition | |
|---|---|
| Compound of formula I, e.g., (3R,4R)-N-[2-[7-[4-[4-[3-(2-Methoxy-benzyloxy)-propoxy]-phenyl]-piperidin-3-yloxymethyl]-3,4-dihydro-2H-quinolin-1-yl]-ethyl]-acetamide | 3.0 mg |
| Sodium glycocholate | 98.5 mg |
| Soya lecithin | 158.2 mg |
| Sodium dihydrogen phosphate | 1.8 mg |
| Disodium-hydrogen phosphate | 9.5 mg |
| Water for injection purposes | ad 1.0 ml |

Production

The compound of formula I, sodium glycocholate and soya lecithin are dissolved in the required amount of ethanol (or an adequate volatile solvent). The solvent is evaporated under reduced pressure and slight heating. The residue is dissolved in the buffered aqueous phase. The solution is processed by conventional procedures.

| Example C: Tablets | |
|---|---|
| Composition | |
| 1) Compound of formula I, e.g., (3R,4R)-N-[2-[7-[4-[4-[3-(2-Methoxy-benzyloxy)-propoxy]-phenyl]-piperidin-3-yloxymethyl]-3,4-dihydro-2H-quinolin-1-yl]-ethyl]-acetamide | 200 mg |
| 2) Anhydrous lactose | 160 mg |
| 3) Hydroxypropylmethylcellulose | 18 mg |
| 4) Sodium-carboxymethylcellulose | 20 mg |
| 5) Magnesium stearate | 2 mg |
| Tablet weight | 400 mg |

Production 1) and 2) are mixed intensively. The mixture is thereafter moistened with an aqueous solution of 3) and kneaded, and the resulting mass is granulated, dried and sieved. The granulate is mixed with 4) and 5) and pressed to tablets of suitable size.

Upon reading the present specification various alternative embodiments will become obvious to the skilled artisan. These variations are to be considered within the scope and spirit of the subject invention, which is only to be limited by the claims that follow and their equivalents.

What is claimed is:

1. A compound of formula:

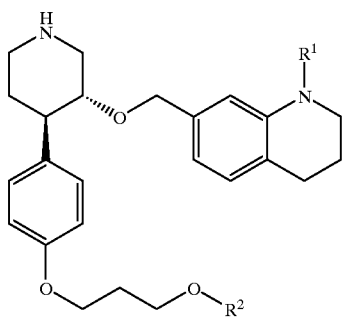

I wherein $R^1$ is a) $-(CH_2)_k-N(R^3, R^4)$, wherein k is 2, 3 or 4;
b) $-(CH_2)_k-O-R^3$, wherein k is 2, 3 or 4;
c) $-(CH_2)_m-R^5$, wherein m is 1 or 2; or
d) $-(CH_2)_l-R^6$, wherein l is 1, 2 or 3;

$R^2$ is lower cycloalkylalkyl, 1,1,1-trifluoroethyl, phenyl, benzyl, phenyl substituted independently with from one to three halogen, cyano, $C_1-C_3$-alkoxy, or nitro groups, or benzyl substituted independently with from one to three halogen, cyano, $C_1-C_3$-alkoxy, or nitro groups;

$R^3$ is hydrogen or $C_1-C_3$-alkyl;

$R^4$ is hydrogen, $C_1-C_3$-alkyl, $C_1-C_3$-alkylsulfonyl, aminosulfonyl, $C_1-C_3$-alkylaminosulfonyl, $C_1-C_3$-alkylaminocarbonyl, $C_1-C_3$-alkylcarbonyl, trifluoromethylcarbonyl, trifluoromethylsulfonyl, or aminocarbonyl;

$R^5$ is $C_1-C_3$-alkoxycarbonyl, aminocarbonyl, $C_1-C_3$-alkylaminocarbonyl, di-$C_1-C_3$-alkylaminocarbonyl, or cyano;

$R^6$ is imidazolyl or triazolyl, with the proviso that l must be 2 or 3 if the imidazolyl or triazolyl is bound via a C—N-bond;

or a pharmaceutically acceptable salt thereof.

2. The compound according to claim 1, wherein $R^1$ is $-(CH_2)_k-N(R^3, R^4)$ and wherein k is 2, 3 or 4.

3. The compound according to claim 2, wherein $R^1$ is $-(CH_2)_2-N(R^3, R^4)$.

4. The compound according to claim 3, wherein $R^1$ is ethylacetamide.

5. The compound according to claim 2, wherein $R^3$ is hydrogen.

6. The compound according to claim 1, wherein $R^1$ is $-(CH_2)_k-O-R^3$ and wherein k is 2, 3 or 4.

7. The compound according to claim 6, wherein $R^1$ is $-(CH_2)_2-O-R^3$ or $-(CH_2)_3-O-R^3$.

8. The compound according to claim 7, wherein $R^1$ is methoxypropyl.

9. The compound according to claim 7, wherein $R^1$ is hydroxypropyl.

10. The compound according to claim 6, wherein $R^3$ is hydrogen or $C_1-C_3$-alkyl.

11. The compound according to claim 10, wherein $R^3$ is hydrogen.

12. The compound according to claim 10, wherein $R^3$ is $C_1-C_3$-alkyl.

13. The compound according to claim 1, wherein $R^1$ is $-(CH_2)_m-R^5$, wherein m is 1 or 2.

14. The compound according to claim 1, wherein $R^1$ is $-(CH_2)_l-R^6$, wherein l is 1, 2 or 3.

15. The compound according to claim 1, wherein $R^2$ is benzyl or benzyl substituted independently with from one to three halogen, cyano, $C_1-C_3$-alkoxy, or nitro groups.

16. The compound according to claim 15, wherein $R^2$ is benzyl or benzyl substituted independently with from one to three $C_1-C_3$-alkoxy groups.

17. The compound according to claim 16, wherein $R^2$ is benzyl substituted with one $C_1-C_3$-alkoxy group.

18. The compound according to claim 15, wherein $R^2$ is benzyl or benzyl substituted independently with from one to three $C_1-C_3$-alkoxy groups or halogen.

19. The compound according to claim 15, wherein $R^2$ is benzyl substituted independently with one $C_1-C_3$-alkoxy group and from one to three halogen.

20. The compound according to claim 1, wherein $R^4$ is hydrogen or $C_1-C_3$-alkyl.

21. The compound according to claim 1, wherein $R^4$ is $C_1-C_3$-alkylsulfonyl, aminosulfonyl, $C_1-C_3$-alkylaminosulfonyl, $C_1-C_3$-alkylaminocarbonyl, $C_1-C_3$-alkylcarbonyl, trifluoromethylcarbonyl, trifluoromethylsulfonyl, or aminocarbonyl.

22. The compound according to claim 21, wherein $R^4$ is $C_1-C_3$-alkylsulfonyl, aminosulfonyl, $C_1-C_3$-alkylcarbonyl, trifluoromethylcarbonyl, trifluoromethylsulfonyl, or aminocarbonyl.

23. The compound according to claim 22, wherein $R^4$ is methanesulfonyl, aminosulfonyl, acetyl, trifluoroacetyl, trifluoromethanesulfonyl, or aminocarbonyl.

24. The compound according to claim 22, wherein $R^4$ is $C_1-C_3$-alkylcarbonyl.

25. The compound according to claim 23, wherein $R^4$ is acetyl.

26. The compound according to claim 1, wherein $R^5$ is $C_1-C_3$-alkoxycarbonyl, aminocarbonyl, $C_1-C_3$-alkylaminocarbonyl, di-$C_1-C_3$-alkylaminocarbonyl.

27. The compound according to claim 1, wherein $R^5$ is cyano.

28. The compound according to claim 26, wherein $R^5$ is aminocarbonyl.

29. The compound according to claim 1, wherein $R^6$ is imidazolyl, with the proviso that l must be 2 or 3 if the imidazolyl is bound via a C—N-bond.

30. The compound according to claim 1, wherein $R^6$ is triazolyl, with the proviso that l must be 2 or 3 if the triazolyl is bound via a C—N-bond.

31. The compound according to claim 1, wherein $R^2$ is benzyl substituted with $C_1$–$C_3$-alkoxy.

32. The compound according to claim 31, wherein $R^2$ is methoxybenzyl.

33. The compound according to claim 32, wherein $R^2$ is 2-methoxybenzyl.

34. The compound according to claim 33, wherein $R^1$ is —$(CH_2)_k$—$N(R^3,R^4)$ and wherein k is 2, 3 or 4.

35. The compound according to claim 34, wherein $R^3$ is hydrogen.

36. The compound according to claim 35, wherein $R^4$ is hydrogen.

37. The compound according to claim 36, wherein k is 2.

38. The compound according to claim 37 which is (3R, 4R)-2-[7-[4-[4-[3-(2-methoxy-benzyloxy)propoxy]-phenyl]-piperidin-3-yloxymethyl]-3,4-dihydro-2H-quinolin-1-yl]-ethylamine.

39. The compound according to claim 36, wherein k is 3.

40. The compound according to claim 39 which is (3R, 4R)-3-[7-(4-[4-[3-(2-methoxy-benzyloxy)-propoxy]-phenyl]-piperidin-3-yloxymethyl)-3,4-dihydro-2H-quinolin-1-yl]-propylamine.

41. The compound according to claim 36, wherein k is 4.

42. The compound according to claim 41 which is (3R, 4R)-4-[7-(4-[4-[3-(2-methoxy-benzyloxy)-propoxy]-phenyl]-piperidin-3-yloxymethyl)-3,4-dihydro-2H-quinolin-1-yl]-butylamine.

43. The compound according to claim 35, wherein $R^4$ is $C_1$–$C_4$-alkyl.

44. The compound according to claim 43, wherein $R^4$ is methyl.

45. The compound according to claim 44, wherein k is 2.

46. The compound according to claim 45 which is (3R, 4R)-[2-[7-[4-[4-[3-(2-methoxy-benzyloxy)-propoxy]-phenyl]-piperidin-3-yloxymethyl]-3,4-dihydro-2H-quinolin-1-yl]-ethyl]-methyl-amine.

47. The compound according to claim 44, wherein k is 3.

48. The compound according to claim 47 which is (3R, 4R)-[3-[7-[4-[4-[3-(2-methoxy-benzyloxy)-propoxy]-phenyl]-piperidin-3-yloxymethyl]-3,4-dihydro-2H-quinolin-1-yl]-propyl]-methyl-amine.

49. The compound according to claim 35, wherein $R^4$ is $C_1$–$C_3$-alkylcarbonyl.

50. The compound according to claim 49, wherein $R^4$ is methylcarbonyl.

51. The compound according to claim 50, wherein k is 2.

52. The compound according to claim 51 which is (3R, 4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide.

53. The compound according to claim 50, wherein k is 3.

54. The compound according to claim 53 which is (3R, 4R)-N-[3-[7-(4-[4-[3-(2-methoxy-benzyloxy)-propoxy]-phenyl]-piperidin-3-yloxymethyl)-3,4-dihydro-2H-quinolin-1-yl]-propyl]-acetamide.

55. The compound according to claim 35, wherein $R^4$ is $C_1$–$C_3$-alkylsulfonyl.

56. The compound according to claim 55, wherein $R^4$ is methylsulfonyl.

57. The compound according to claim 56, wherein k is 2.

58. The compound according to claim 57 which is (3R, 4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]methanesulfonamide.

59. The compound according to claim 35, wherein $R^4$ is aminosulfonyl.

60. The compound according to claim 59, wherein k is 2.

61. The compound according to claim 60 which is (3R, 4R)-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-sulfamide.

62. The compound according to claim 35, wherein $R^4$ is aminocarbonyl.

63. The compound according to claim 62, wherein k is 2.

64. The compound according to claim 63 which is (3R, 4R)-[[2-[7-[4-[4-[3-(2-methoxy-benzyloxy)-propoxy]-phenyl]-piperidin-3-yloxymethyl]-3,4-dihydro-2H-quinolin-1-yl]-ethyl]-urea.

65. The compound according to claim 35, wherein $R^4$ is trifluoromethylcarbonyl.

66. The compound according to claim 65, wherein k is 2.

67. The compound according to claim 66 which is (3R, 4R)-2,2,2-trifluoro-N-[2-[7-[4-[4-[3-(2-methoxy-benzyloxy)-propoxy]-phenyl]-piperidin-3-yloxymethyl]-3,4-dihydro-2H-quinolin-1-yl]-ethyl]-acetamide.

68. The compound according to claim 34, wherein $R^3$ is $C_1$–$C_3$-alkyl.

69. The compound according to claim 68, wherein $R^4$ is $C_1$–$C_3$-alkyl.

70. The compound according to claim 69, wherein $R^3$ and $R^4$ are both methyl.

71. The compound according to claim 70, wherein k is 2.

72. The compound according to claim 71 which is (3R, 4R)-[2-[7-(4-[4-[3-(2-methoxy-benzyloxy)-propoxy]-phenyl]-piperidin-3-yloxymethyl)-3,4-dihydro-2H-quinolin-1-yl]-ethyl]-dimethyl-amine.

73. The compound according to claim 33, wherein $R^1$ is —$(CH_2)_k$—O—$R^3$, wherein k is 2, 3 or 4.

74. The compound according to claim 73, wherein $R^3$ is hydrogen.

75. The compound according to claim 74, wherein k is 2.

76. The compound according to claim 75 which is (3R, 4R)-2-[7-[4-[4-[3-(2-methoxy-benzyloxy)-propoxy]-phenyl]-piperidin-3-yloxymethyl]-3,4-dihydro-2H-quinolin-1-yl]-ethanol.

77. The compound according to claim 74, wherein k is 3.

78. The compound according to claim 77 which is (3R, 4R)-3-[7-[4-[4-[3-(2-methoxy-benzyloxy)-propoxy]-phenyl]-piperidin-3-yloxymethyl]-3,4-dihydro-2H-quinolin-1-yl]-propan-1-ol.

79. The compound according to claim 73, wherein $R^3$ is $C_1$–$C_3$-alkyl.

80. The compound according to claim 79, wherein $R^3$ is methyl.

81. The compound according to claim 80, wherein k is 2.

82. The compound according to claim 81 which is (3R, 4R)-7-[4-[4-[3-(2-methoxy-benzyloxy)-propoxy]-phenyl]-piperidin-3-yloxymethyl]-1-(2-methoxy-ethyl)-1,2,3,4-tetrahydro-quinoline.

83. The compound according to claim 80, wherein k is 3.

84. The compound according to claim 83 which is (3R, 4R)-7-[4-[4-[3-(2-methoxy-benzyloxy)-propoxy]-phenyl]-piperidin-3-yloxymethyl)-1-(3-methoxy-propyl]-1,2,3,4-tetrahydro-quinoline.

85. The compound according to claim 33, wherein $R^1$ is —$(CH_2)_m$—$R^5$, wherein m is 1 or 2.

86. The compound according to claim 85, wherein m is 1.

87. The compound according to claim 86, wherein $R^5$ is $C_1$–$C_3$-alkoxycarbonyl.

88. The compound according to claim 87, wherein $R^5$ is methoxycarbonyl.

89. The compound according to claim 88 which is (3R, 4R)-[7-(4-[4-[3-(2-methoxy-benzyloxy)-propoxy]-phenyl]-piperidin-3-yloxymethyl)-3,4-dihydro-2H-quinolin-1-yl]-acetic acid methyl ester.

90. The compound according to claim 87, wherein $R^5$ is ethoxycarbonyl.

91. The compound according to claim 90 which is (3R, 4R)-[7-(4-[4-[3-(2-methoxy-benzyloxy)-propoxy]-phenyl]-piperidin-3-yloxymethyl)-3,4-dihydro-2H-quinolin-1-yl]-acetic acid ethyl ester.

92. The compound according to claim 86, wherein $R^5$ is aminocarbonyl.

93. The compound according to claim 92 which is (3R, 4R)-2-[7-[4-[4-[3-(2-methoxy-benzyloxy)-propoxy]-phenyl]-piperidin-3-yloxymethyl-3,4-dihydro-2H-quinolin-1-yl]-acetamide.

94. The compound according to claim 86, wherein $R^5$ is cyano.

95. The compound according to claim 94 which is (3R, 4R)-[7-(4-[4-[3-(2-methoxy-benzyloxy)-propoxy]-phenyl]-piperidin-3-yloxymethyl)-3,4-dihydro-2H-quinolin-1-yl]-acetonitrile.

96. The compound according to claim 85, wherein m is 2.

97. The compound according to claim 96, wherein $R^5$ is $C_1$-$C_3$-alkoxycarbonyl.

98. The compound according to claim 97, wherein $R^5$ is methoxycarbonyl.

99. The compound according to claim 98 which is (3R, 4R)-3-[7-(4-[4-[3-(2-methoxy-benzyloxy)-propoxy]-phenyl]-piperidin-3-yloxymethyl)-3,4-dihydro-2H-quinolin-1-yl]-propionic acid methyl ester.

100. The compound according to claim 33, wherein $R^1$ is —$(CH_2)_l$—$R^6$, wherein l is 1, 2 or 3.

101. The compound according to claim 100, wherein l is 2 or 3.

102. The compound according to claim 101, wherein l is 2.

103. The compound according to claim 100, wherein $R^6$ is imidazolyl.

104. The compound according to claim 103 which is (3R,4R)-1-(2-imidazol-1-yl-ethyl)-7-(4-]4-[3-(2-methoxy-benzyloxy)-propoxy]-phenyl]-piperidin-3-yloxymethyl)-1,2,3,4-tetrahydro-quinoline.

105. The compound according to claim 1, wherein $R^1$ is —$(CH_2)_k$—O—$R^3$, wherein k is 2, 3 or 4.

106. The compound according to claim 1, wherein $R^3$ is $C_1$-$C_3$-alkyl.

107. The compound according to claim 106, wherein $R^3$ is methyl.

108. The compound according to claim 107, wherein k is 3.

109. The compound according to claim 108, wherein $R^2$ is lower cycloalkylalkyl.

110. The compound according to claim 109, wherein $R^2$ is lower cyclopropylmethyl.

111. The compound according, to claim 110 which is (31R,4R)-7-[4-[4-(3-cyclopropylmethoxy-propoxy)-phenyl]-piperidin-3-yloxymethyl]-1-(3-methoxy-propyl)-1,2,3,4-tetrahydro-quinoline.

112. The compound according to claim 108, wherein $R^2$ is 1,1,1-trifluoroethyl.

113. The compound according to claim 112 which is (3R,4R)-1-(3-methoxy-propyl)-7-[4-[4-[3-(2,2,2-trifluoro-ethoxy)-propoxy]-phenyl]-piperidin-3-yloxymethyl]-1,2,3,4-tetrahydro-quinoline.

* * * * *

UNITED STATES PATENT AND TRADEMARK OFFICE
CERTIFICATE OF CORRECTION

PATENT NO.   : 6,197,959 B1
DATED        : March 6, 2001
INVENTOR(S)  : Volker Breu, Daniel Bur, Hans-Peter Märki, Eric Vieira, Wolfgang Wostl It is certified that error appears in the above-identified patent and that said Letters Patent is hereby corrected as shown below:

Column 36, claim 104,
Line 8, delete "(3R,4R)-1-(2-imidazol-1-yl-ethyl)-7-(4-]4-[3-(2-methoxy-benzyloxy)-propoxy]-phenyl]-piperidin-3-yloxymethyl)-1,2,3,4-tetrahydro-quinoline" and insert -- (3R,4R)-1-(2-imidazol-1-yl-ethyl)-7-(4-[4-[3-(2-methoxy-benzyloxy)-propoxy]-phenyl]-piperidin-3-yloxymethyl)-1,2,3,4-tetrahydro-quinoline --.

Column 36, claim 111,
Line 23, delete "(31R,4R)-7-[4-[4-(3-cyclopropylmethoxy-propoxy)-phenyl]-piperidin-3-yloxymethyl]-1-(3-methoxy-propyl)-1,2,3,4-tetrahydro-quinoline" and insert -- (3R,4R)-7-[4-[4-(3-cyclopropylmethoxy-propoxy)-phenyl]-piperidin-3-yloxymethyl]-1-(3-methoxy-propyl)-1,2,3,4-tetrahydro-quinoline --.

Signed and Sealed this

Thirteenth Day of November, 2001

Attest:

NICHOLAS P. GODICI
Attesting Officer    Acting Director of the United States Patent and Trademark Office